US012685778B2

(12) United States Patent
Esteve et al.

(10) Patent No.: US 12,685,778 B2
(45) Date of Patent: Jul. 21, 2026

(54) NANO-ASSEMBLIES OF CONJUGATES OF RETINOIDS AND AMINO ACIDS

(71) Applicants: Xabier Murgia Esteve, Berango (ES); Duy-Khiet Ho, Seattle, WA (US)

(72) Inventors: Xabier Murgia Esteve, Berango (ES); Duy-Khiet Ho, Seattle, WA (US)

( * ) Notice: Subject to any disclaimer, the term of this patent is extended or adjusted under 35 U.S.C. 154(b) by 508 days.

(21) Appl. No.: 18/548,612

(22) PCT Filed: Nov. 17, 2021

(86) PCT No.: PCT/EP2021/082037

§ 371 (c)(1),
(2) Date: Sep. 1, 2023

(87) PCT Pub. No.: WO2022/184295

PCT Pub. Date: Sep. 9, 2022

(65) Prior Publication Data

US 2024/0189431 A1 Jun. 13, 2024

(30) Foreign Application Priority Data

Mar. 1, 2021 (EP) .................................... 21160026

(51) Int. Cl.
*A61K 31/07* (2006.01)
*A61K 47/54* (2017.01)
*A61K 47/55* (2017.01)

(52) U.S. Cl.
CPC ............ *A61K 47/551* (2017.08); *A61K 31/07* (2013.01); *A61K 47/542* (2017.08)

(58) Field of Classification Search
CPC .... A61K 47/551; A61K 47/542; A61K 37/07; A61P 17/00; A61P 11/00
See application file for complete search history.

(56) References Cited

PUBLICATIONS

International Search Report and Written Opinion for International Patent Application No. PCT/EP2021/082037, mailed Sep. 9, 2022.
Livnah Nurit et al: "Model Compounds Can Mimic Spectroscopic Properties of Bovine Rhodopsin," J. Am. Chem. Soc, vol. 115, No. 1, Jan. 1, 1993, pp. 351-353, XP55828275.
Kim Hye Jin et al: "Vitamin A aldehyde-taurine adduct and the visual cycle," Proceedings of the National Academy of Sciences, vol. 117, No. 40, Sep. 21, 2020, pp. 24867-24875, XP55827987.
Doll Tais A P F et al: "Nanoscale assemblies and their biomedical applications," Journal of the Royal Society. Interface, The Royal Society, London, GB, vol. 10, No. 80, Mar. 6, 2013, Article No. 20120740, XP008173961.

*Primary Examiner* — Sikarl A Witherspoon
(74) *Attorney, Agent, or Firm* — Jordan IP Law, LLC

(57) ABSTRACT

The present invention relates to nano-assemblies of conjugates of retinoids and amino acids, to uses thereof, and to methods of making the same.

18 Claims, 2 Drawing Sheets

NANO-ASSEMBLIES OF CONJUGATES OF RETINOIDS AND AMINO ACIDS

CROSS REFERENCE TO RELATED APPLICATIONS

This application is the US National stage Application under 35 U.S.C. § 371 of International Patent Application No. PCT/EP2021/082037 filed on Nov. 17, 2021, which claims benefit of and priority to European Patent Application No. 21160026.7, filed on Mar. 1, 2021, the contents of which are incorporated by reference in its entirety.

The present invention relates to nano-assemblies of conjugates of retinoids and amino acids, to uses thereof, and to methods of making the same.

Retinoids are a class of chemical compounds including retinol and retinol esters (also called retinyl esters) as well as retinal, retinoic acid, isotretinoin, alitretinoin and chemically related compounds. Retinol is also referred to as vitamin A1. Likewise, retinol esters are also referred to as vitamin A esters, retinal is also referred to as vitamin A aldehyde, and retinoic acid is also referred to as vitamin A acid. Vitamin A1, vitamin A esters, vitamin A aldehyde, vitamin A acids, and chemically related compounds are also collectively referred to as "vitamin A". Retinol esters, retinol, retinal can be converted into each other by enzymatic reactions. Furthermore, retinol esters, retinol and retinal can be converted into retinoic acids by enzymatic reactions. However, retinoic acids cannot be converted into retinol esters, retinol or retinal by enzymatic reactions.

Vitamin A and its chemically related compounds play a relevant role principally by controlling gene expression. Among others, vitamin A plays a relevant role in the regulation of the vision, the modulation of the immune system, embryological development, normal growth of the bones, differentiation of several epithelia throughout the human body such as the eye epithelium, genitor-urinary tract, teeth, respiratory tract, and skin, and antioxidant function. With such a ubiquitous presence in different organ systems, vitamin A deficiency, which may, in turn, be a primary deficiency due to a low intake or a secondary deficiency due to the fast depletion of endogenous reservoirs in disease states, is often associated with several of pathologies.

In the lungs, vitamin A is involved in the proliferation, repair and overall homeostasis of epithelial cells. For instance, animal models have shown that maternal vitamin A deprivation leads to agenesis (i.e. lung underdevelopment) and sustained deprivation after birth leads to arrested lung development predisposing the lungs to several pulmonary conditions. Prematurely-born newborns are prone to pulmonary infections and often develop chronic lung disease and arrested development (i.e. bronchopulmonary dysplasia, BPD) due to mechanical ventilation in combination with relatively high oxygen levels. Premature infants have lower plasma retinol concentrations compared with term infants and its supplementation at birth reduces mortality, and may reduce the incidence of BPD. Preclinical studies in premature lambs managed with mechanical ventilation have shown that daily, intramuscular vitamin A supplementation increased alveolar secondary septation, decreased thickness of the mesenchymal tissue at distal air space walls, and increased alveolar capillary growth. Similarly, intramuscular vitamin A supplementation significantly reduced the incidence of BPD in a clinical study.

Retinoids are also required for the maintenance of alveolar homeostasis in adulthood. In pulmonary infections, plasma retinol levels are markedly reduced, promoting susceptibility to further cyclic infections. Similarly, there is an inverse correlation between serum retinol levels and the pulmonary obstruction of asthmatic patients. Chronic obstructive pulmonary disease (COPD) accounted for 3 million deaths in 2016 and is considered the third cause of mortality worldwide by the World Health Organization. COPD results from chronic bronchitis and emphysema (destruction of the inner alveolar wall that reduces the number of gas exchange units). Experimental studies have shown that reduced vitamin A dietary intake is associated with emphysema that develops through alterations of the extracellular matrix remodelling. Nevertheless, de novo synthesis of new alveoli (i.e. alveologenesis) has been demonstrated in adult rats following treatment with retinoic acid, which reveals the potential of retinoids in lung regeneration. The disruption of the homeostasis of the extracellular matrix is also the main cause of lung fibrosis, a condition that progressively replaces functional lung epithelium with fibrotic tissue. Such extracellular matrix imbalances are also believed to be the underlying mechanisms that distort and damage several other epithelia and organ systems in the human body.

In the skin, matrix metalloproteinases play an essential role in the remodelling of the extracellular matrix, which in turn provides structural integrity to the skin. For instance, photodamage (i.e. chronic exposure to UV light) is characterized by collagen degradation and the accumulation of abnormal elastotic material, alterations of blood vessels, and an increase of reactive oxygen species accompanied by lower synthesis of endogenous antioxidant enzymes. External as well as endogenous biochemical imbalances that are deleterious to the skin's normal regulation may give rise to many dermatological conditions, including chronic and severe acne, different types of psoriasis, neoplasms, and skin cancer. In this regard, retinoids, and in particular retinoid acids, are indicated for the topical treatment of a wide range of dermatological diseases including chronic and severe acne, acne conglobate, psoriasis (including plaque psoriasis, pustular psoriasis, napkin psoriasis, guttate psoriasis, erythrodermic psoriasis, seborrheic-like psoriasis, and psoriatic arthritis), photoaging, skin cancer, actinic keratosis, preneoplasm disorders, initial neoplasm, multiple neoplasms, ichthyosis, melasma, and lichen planus. Also, retinoids may find an application in other dermatological diseases like HIV-associated Kaposi sarcoma, genodermatosis (ichthyosis), pitiriasis rubra pilaris, hypertrophic scar, rosacea, chronic hyperkeratosis, mucosal keratinization, neoplasms (e.g. Lymphoma of the skin), hair loss conditions (alopecia), wound healing, skin pigmentation disorders, stretch marks on the skin, viral infections, xerophthalmia; actinic keratosis, oral leukoplakia, xeroderma pigmentosum, nevoid basal-cell carcinoma, basal-cell carcinoma, Darier's disease, confluent and reticulated papillomatosis, atrophoderma vermiculatum, ulerythema ophryogenes, palmoplantar keratoderma, Papillon-Lefèvre syndrome, Vohwinkel syndrome, acanthosis nigricans, Muir-Torre syndrome, Cowden's disease, cutaneous T cell lymphoma, histiocytosis of Langerhans cells, oral leukoplakia, Bowen's disease, erythroplasia of Queirat, metastatic melanoma, skin cancer in transplanted patients, cutaneous sarcoidosis, granuloma annulare, O'brien's actinic granuloma, siliconoma, rosacea, rosacea fulminans, solid cutaneous edema, rhinophyma, cutaneous disseminated lupus, cystic acne, steatocystoma multiplex, hidradenitis suppurativa, ofuji's syndrome, multiple syringomas, actinic folliculitis, sclerosing folliculitis of the neck, keratosis pilaris, folliculitis decalvans, folliculitis by pityrosporum, folliculitis by Gram negative, recurrent folliculitis, genital wart, scleroderma, alopecia mucinosa, discoid lupus erythematosus, systemic scleroderma, chronic lichenoid keratosis, lichen-like diseases, infectious diseases, and pyogenic granuloma.

Due to the beneficial effects of retinoids in the skin, their use, in particular the use of retinol and retinyl esters, is also prevalent in skincare and cosmetic products and can be found in face and eye creams, body lotions, sun lotions, lip products and baby creams, serums, sprays, ampoules, or several other formats. The main applications of retinoids in this field relate to wound healing, wound management and dressing, management and elimination of stretch marks on the skin (striae), treatment of androgenetic alopecia, management of smooth wrinkles and fine lines, and anti-ageing products, among others.

The high potential of retinoids for the treatment of pulmonary, skin, and other organ system diseases is limited by the difficulty to achieve a stable formulation of vitamin A derivatives. Chemically, retinoids are unstable upon contact with $O_2$ and light. Furthermore, retinoids are not water-soluble molecules as they are highly hydrophobic. Also, they are quickly hydrolyzed upon being exposed to aqueous media.

The conventional formulations of retinoids usually consist of the dissolution of retinoids in an oily mixture, organic solvent and aqueous media mixture, or a water-in-oil emulsion. The oily combination is referred to as the mixture of lipids that can dissolve retinoids. The organic solvent and water mixture is referred to the employment of organic solvent, e.g. ethanol, dimethyl sulfoxide (DMSO), in enhancing the solubility of retinoids in aqueous media. For instance, vitamin A formulations for preclinical studies evaluating the pulmonary outcomes of rodents have used canola oil or cottonseed oil to solubilize retinoids, which were applied directly to the mouth of the animals or injected intraperitoneally. Due to the lack of available formulations, late-stage preclinical studies evaluating the pulmonary outcomes of premature lambs have used commercially available nutritional supplement products, such as Aquasol A parenteral® or NovaSOL®, which were experimentally administered intramuscularly, intravenously or intratracheally. Pulmonary application of vitamin A has only been investigated experimentally through the endotracheal route since there is not yet a vitamin A formulation available that will further enable the aerosol delivery by nebulization. In one study, retinyl acetate was first dissolved in alcohol and then mixed with the bovine lung extract surfactant (BLES), mainly composed of phospholipids, to be delivered as an intratracheal bolus.

The aforementioned formulations were developed in the context of preliminary experimental studies and cannot be deemed optimal for human use. The routes of administration of these formulations are significantly limited due to the abundant use of oily mixture or organic solvents. In particular, these formulations cannot be administered as aerosols, intranasally, intratracheally or intravenously in humans. Therefore, clinical trials in the context of BPD have mainly used intramuscular delivery of vitamin A (e.g. mixed with Intralipid lipid emulsion) for the treatment of premature infants.

The topical delivery of retinoids for dermatological conditions and skincare application may be seen as less of a problem due to the possibility to formulate creams, gels, or serums with limited systemic exposure. However, retinoids may produce local skin irritation in the first stages of the treatment. Moreover, the excessive use of lipids or organic solvent is not recommended in the treatment of some diseases, e.g., for topical administration in sensitive skin. Both therapeutic indications with retinoic acids and skincare applications with retinol from high-level cosmetic products recommend the use of retinoids at night due to their susceptibility to light inactivation.

Hence, an innovative strategy to formulate and moreover protect and stabilize retinoids in aqueous media, preferably free of organic solvents, which can be used in different routes of administration, is emergently needed. There have been attempts to provide water-based formulations of retinoids based on micro- and nano-formulation technologies. These technologies include liposomal delivery systems, solid-lipid micro- and nano-particles, polymeric micro- and nano-particles, micellar delivery systems. Retinoids are encapsulated in the hydrophobic compartment of the micro- and nano-sized particles based on hydrophobic interaction and thus can be protected and stabilized from the effects of $O_2$, light and aqueous environment. However, current technologies allow only limited loading weight percentages of retinoids of mostly less than 1%. Furthermore, uniform loading of retinoids has not been achieved, meaning that not all the micro- and nano-sized particles carry retinoids due to the uncontrollable loading mechanism. Moreover, the excessive use of excipients—up to 99 weight percentage or more—that can cause adverse effects is another problem of the current micro- and nano-formulation technologies.

In the case of injection administration, the limited loading weight percentages also increase the injection volume or the used volume of the formulation, and moreover, the excess use of excipients can cause higher viscosity that troubles the injectability and results in discomfort in patients.

Furthermore, the excess use of excipients also results in changes in the properties of the combined therapeutics, for example, surface tension properties, when retinoids are required to co-administered with other agents, for example, surfactants.

It is therefore, an object of the present invention to overcome the problems of the prior art.

The object is solved by the present invention.

In one aspect, the invention relates to a nano-assembly comprising conjugates of the following formula (1)

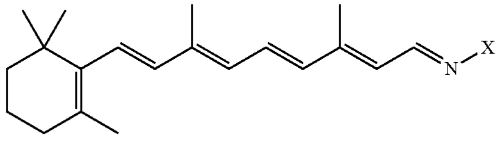

wherein X is selected from the group consisting of

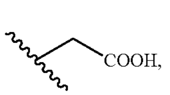
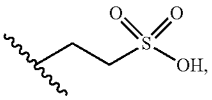
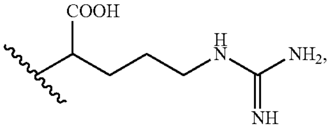
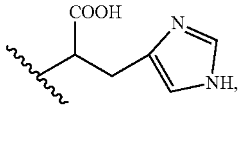
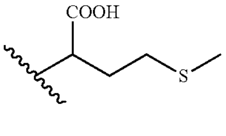
,

-continued

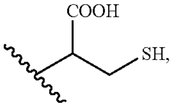 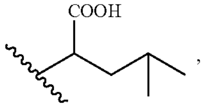

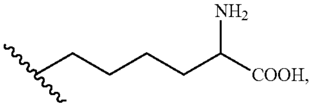 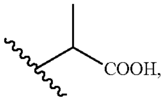

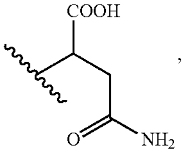 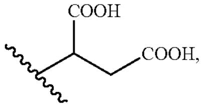

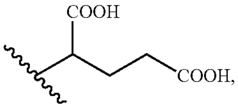 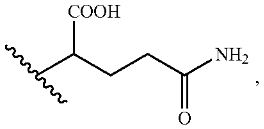

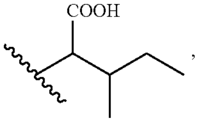 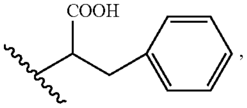

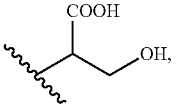 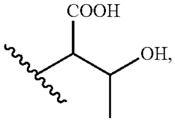

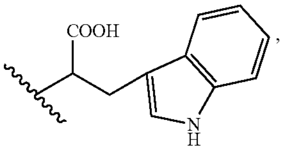

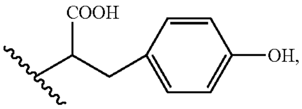 and 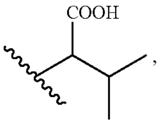

and/or comprising conjugates of the following formula (4)

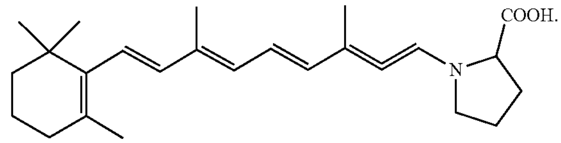 [SMILES: CC(=C=CN1CCCC1C(=O)O)/C=C/C=C(C)/C=C/C1=C(C)CCCC1(C)C]

Preferably, X is selected from the group consisting of from the group consisting of

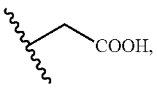 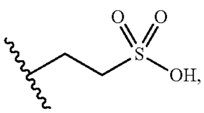

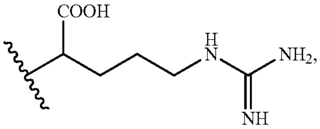 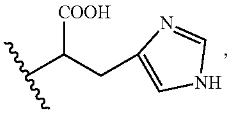

-continued

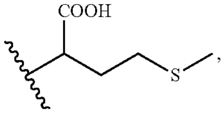 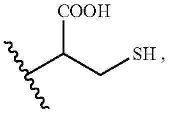

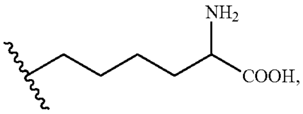 and 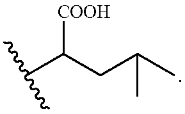

In some embodiments, the nano-assemblies of the present invention comprise conjugates of formula (1). In some embodiments, the nano-assemblies of the invention comprise conjugates of formula (4). In some embodiments, the nano-assemblies of the invention comprise both conjugates of formula (1) and conjugates of formula (4). In some embodiments, the nano-assemblies of the invention do not comprise conjugates of formula (1). In some embodiments, the nano-assemblies of the invention do not comprise conjugates of formula (4).

In some embodiments, the nano-assemblies of the present invention consist of conjugates of formula (1). In some embodiments, the nano-assemblies of the invention consist of conjugates of formula (4). In some embodiments, the nano-assemblies of the invention consist of conjugates of formula (1) and conjugates of formula (4).

The nano-assemblies of the invention may comprise or consist of conjugates of formula (1), wherein X is

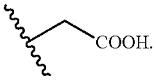

The nano-assemblies of the invention may comprise or consist of conjugates of formula (1), wherein X is

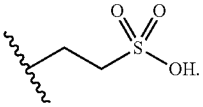 [SMILES: *CCS(=O)(=O)O]

The nano-assemblies of the invention may comprise or consist of conjugates of formula (1), wherein X is

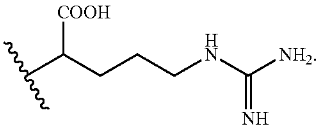 [SMILES: *C(CCCNC(=N)N)C(=O)O]

The nano-assemblies of the invention may comprise or consist of conjugates of formula (1), wherein X is

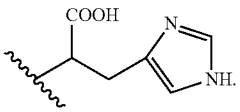 [SMILES: *C(Cc1c[nH]cn1)C(=O)O]

The nano-assemblies of the invention may comprise or consist of conjugates of formula (1), wherein X is

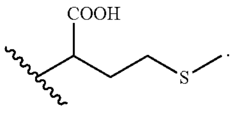 [SMILES: *C(CCSC)C(=O)O]

The nano-assemblies of the invention may comprise or consist of conjugates of formula (1), wherein X is

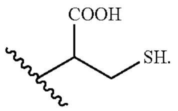 [SMILES: *C(CS)C(=O)O]

The nano-assemblies of the invention may comprise or consist of conjugates of formula (1), wherein X is

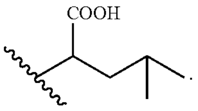 [SMILES: *C(CC(C)C)C(=O)O]

The nano-assemblies of the invention may comprise or consist of conjugates of formula (1), wherein X is

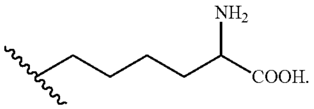 [SMILES: *CCCCC(N)C(=O)O]

The nano-assemblies of the invention may comprise or consist of conjugates of formula (1), wherein X is

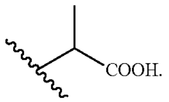 [SMILES: *C(C)C(=O)O]

The nano-assemblies of the invention may comprise or consist of conjugates of formula (1), wherein X is

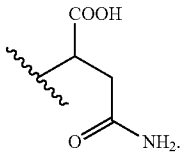

The nano-assemblies of the invention may comprise or consist of conjugates of formula (1), wherein X is

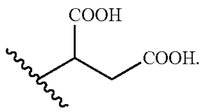 [SMILES: *C(CC(=O)O)C(=O)O]

The nano-assemblies of the invention may comprise or consist of conjugates of formula (1), wherein X is

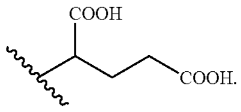 [SMILES: *C(CCC(=O)O)C(=O)O]

The nano-assemblies of the invention may comprise or consist of conjugates of formula (1), wherein X is

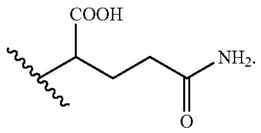 [SMILES: *C(CCC(N)=O)C(=O)O]

The nano-assemblies of the invention may comprise or consist of conjugates of formula (1), wherein X is

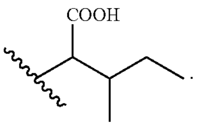 [SMILES: *C(C(=O)O)C(C)CC]

The nano-assemblies of the invention may comprise or consist of conjugates of formula (1), wherein X is

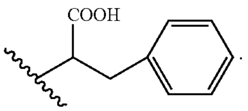

The nano-assemblies of the invention may comprise or consist of conjugates of formula (1), wherein X is

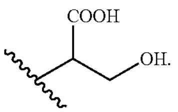 [SMILES: *C(CO)C(=O)O]

The nano-assemblies of the invention may comprise or consist of conjugates of formula (1), wherein X is

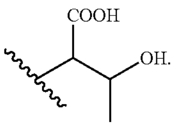 [SMILES: *C(C(=O)O)C(C)O]

The nano-assemblies of the invention may comprise or consist of conjugates of formula (1), wherein X is

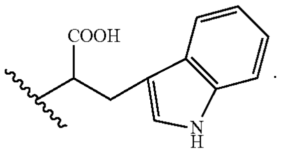 [SMILES: *C(Cc1c[nH]c2ccccc12)C(=O)O]

The nano-assemblies of the invention may comprise or consist of conjugates of formula (1), wherein X is

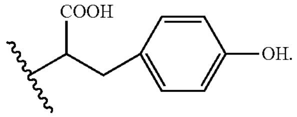 [SMILES: *C(Cc1ccc(O)cc1)C(=O)O]

The nano-assemblies of the invention may comprise or consist of conjugates of formula (1), wherein X is

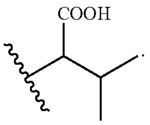 [SMILES: *C(C(=O)O)C(C)C]

The nano-assemblies of the invention may comprise a first type of conjugates of formula (1), wherein X is $X_1$, and further comprise a second type of conjugates of formula (1), wherein X is $X_2$, characterized in that $X_1$ is different from $X_2$. For example, the nano-assemblies of the invention may comprise conjugates of formula (1), wherein X is

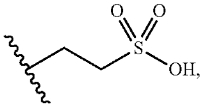 [SMILES: *CCS(=O)(=O)O]

and further comprise conjugates of formula (1), wherein X is

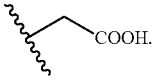 [SMILES: *CC(=O)O]

The nano-assemblies of the invention may consist of conjugates of formula (1), wherein X is

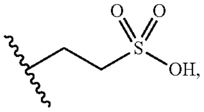 [SMILES: *CCS(=O)(=O)O]

and conjugates of formula (1), wherein X is

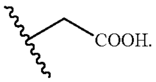

The nano-assemblies of the invention may comprise a first type of conjugates of formula (1), wherein X is $X_1$, and further comprise a second type of conjugates of formula (1), wherein X is $X_2$, and further comprise a third type of conjugates of formula (1), wherein X is $X_3$, characterized in that $X_1$ is different from $X_2$ and $X_3$ and in that $X_2$ is different from $X_3$.

The nano-assemblies of the invention may comprise four or more types of conjugates of formula (1), each type being characterized by having a different X as compared to all other types of conjugates of formula (1) in the nano-assemblies. The nano-assemblies of the invention may comprise up to 20 different types of conjugates of formula (1) in view of the 20 different X residues described herein.

The conjugates of the invention are based on a retinoid and an amino acid being conjugated via an imine or an enamine linkage. The imine (or enamine) linkage is particularly advantageous because it is pH-sensitive. The term "pH-sensitive" indicates that the linkage is not stable at acidic pH-values, in particular at a pH<6.5, for example a pH<6.0, a pH<5.5, or a pH<5.0. Preferably, the term "not stable" indicates that at least 80% of the retinoid is released from the conjugate after incubation at the indicated pH for 8 hours, more preferably for 6 hours, more preferably for 4 hours, more preferably for 2 hours at a temperature of 37° C. The pH-sensitivity is preferably analyzed by proton NMR analysis. The cleavage of the imine (or enamine) bond can be analyzed by proton NMR spectrum. In particular, upon cleavage of the conjugate the corresponding proton peaks of imine bond in the conjugates typically from 8.5 ppm to 9.5 ppm disappear, and the typical peaks of aldehyde group in retinal appear from 9.51 ppm to 10.5 ppm.

A pH-sensitive linking group is particularly advantageous as it enables in vivo cleavage of the conjugate so that the retinoid moiety is set free from the amino acid moiety so that the retinoid moiety is available for various in vivo functions. In particular, cleavage of the conjugate may provide retinal. Retinal can be enzymatically converted into various other retinoids such as retinol, retinol esters and retinoic acids as described above.

Cleavage of the conjugate does not only set free the retinoid moiety but also the amino acid moiety. Amino acids may have various effects as well. The beneficial effects of amino acids generally include antioxidant, anti-inflammatory, anti-aging and anti-toxin effects. The amino acids strengthen immune system, involve in cell signaling, and promote tissue growth and regeneration. In skin care applications, amino acids re-energize and re-hydrate skin, thus are powerful agents for anti-fatigue, anti-aging, and improvement of overall skin appearance. Taurine, in particular, can act as antioxidant, anti-inflammatory, and anti-toxin agent. Taurine can inhibit glycation—one of the main causes of cellular aging—providing anti-aging effects. Furthermore, topical Taurine involves in various pathways to repair damaged skin. Taurine also shows anti-acne and is effective in treating atopic dermatitis and underlying causes of psoriasis. Other examples include arginine, lysine, methionine, histidine, proline, leucine and glycine that protect skin from free-radical damage, restore visible skin damage, strengthen the skin's surface, and reduce signs of aging. In pulmonary applications, amino acids can improve the respiratory health.

Cleavage of a pH-sensitive linkage is exemplarily shown in the following schemes for conjugates of all trans retinal and taurine, as well as all trans retinal and glycine. Notably, taurine and glycine are excipients approved by the U.S. Food and Drug Administration (FDA).

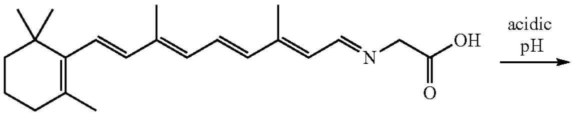

-continued

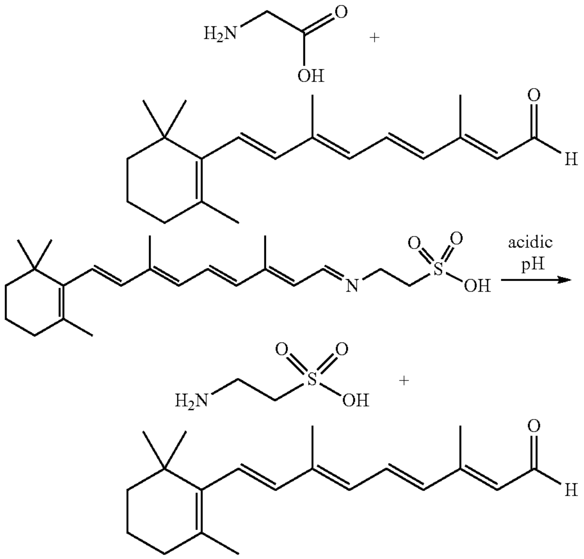

Preferably, the nano-assemblies of the invention consist of the conjugates of formula (1) and/or formula (4). More preferably, the nano-assemblies of the invention consist of the conjugates of formula (1). However, in some embodiments, the nano-assemblies may comprise further conjugates in addition to the conjugates of formula (1) and/or formula (4). Preferably, the sum of the molar amounts of conjugates of formula (1) and formula (4) is at least 5 Mol %, more preferred at least 10 Mol %, more preferred at least 20 Mol %, more preferred at least 30 Mol %, more preferred at least 40 Mol %, more preferred at least 50 Mol %, more preferred at least 60 Mol %, more preferred at least 70 Mol %, more preferred at least 80 Mol %, more preferred at least 90 Mol %, more preferred at least 95 Mol %, more preferred at least 98 Mol %, more preferred at least 99 Mol % as compared to the total molar amount of conjugates constituting the nano-assembly. More preferably, the total molar amount of conjugates of formula (1) is at least 5 Mol %, more preferred at least 10 Mol %, more preferred at least 20 Mol %, more preferred at least 30 Mol %, more preferred at least 40 Mol %, more preferred at least 50 Mol %, more preferred at least 60 Mol %, more preferred at least 70 Mol %, more preferred at least 80 Mol %, more preferred at least 90 Mol %, more preferred at least 95 Mol %, more preferred at least 98 Mol %, more preferred at least 99 Mol % as compared to the total molar amount of conjugates constituting the nano-assembly.

In embodiments of the invention, the nano-assemblies may comprise additional conjugates, in particular conjugates based on a retinoid and an amino acid being conjugated via a linkage that is not pH-sensitive, such as for example an amine linkage. A linkage being "not pH-sensitive" indicates that the linkage is stable at acidic pH-values, in particular at a pH<6.5, for example a pH<6.0, a pH<5.5, or a pH<5.0. Preferably, the term "stable" indicates that less than 80% of the retinoid is released from the conjugate after incubation at the indicated pH for 8 hours, more preferably for 6 hours, more preferably for 4 hours, more preferably for 2 hours at a temperature of 37° C.

Notably, conjugates comprising a retinoid moiety may have advantageous effects even if the linkage to the further moiety is not cleaved. In particular, the retinoid moiety may have antioxidant effects even when still bound to the other moiety. Furthermore, the additional conjugates that are based on a linkage that is not pH-sensitive may be advantageous for further stabilizing the conjugates.

Preferably, additional conjugates are selected from the group consisting of conjugates of the following formula (5)

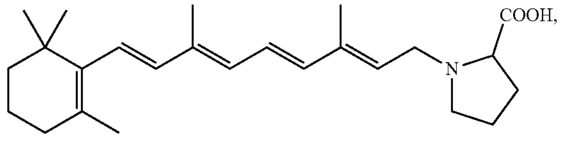 [SMILES: CC1=C(/C=C/C(C)=C/C=C/C(C)=C/CN2CCCC2C(=O)O)C(C)(C)CCC1]

conjugates of the following formula (6)

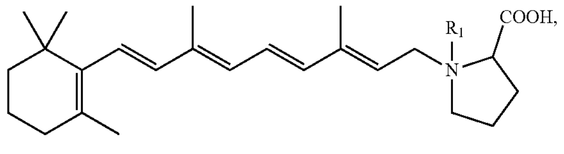

conjugates of the following formula (2)

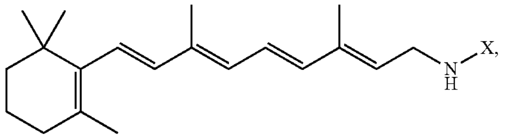

conjugates of the following formula (3)

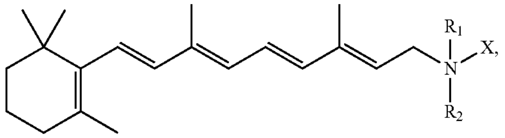

and combinations of two or more thereof, wherein X is selected from the group consisting of

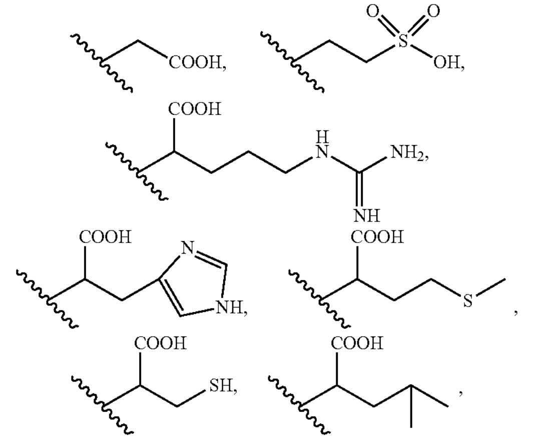

-continued

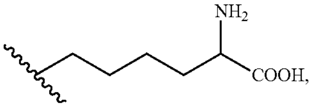 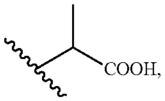

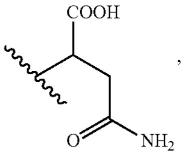, 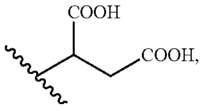

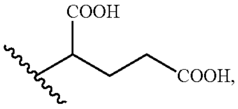 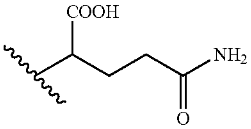,

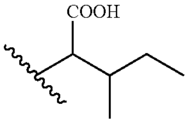, 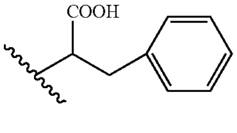,

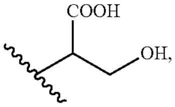 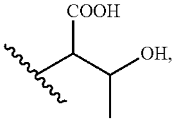

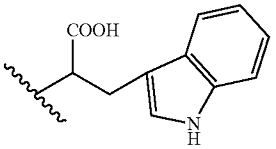,

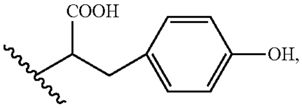 and 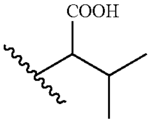, and wherein $R_1$ and $R_2$ are independently selected from the group consisting of —H, —$CH_3$, —$CH_2CH_3$, and —$CH_2CH_2$—(O—$CH_2CH_2$)$_m$—$R_3$, wherein m is in a range of from 1 to 20, for example from 1 to 5, and wherein $R_3$ is selected from the group consisting of —H, —OH, —$NH_2$, —SH, —COOH, and —$OCH_3$.

Preferably, X is selected from the group consisting of

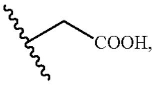 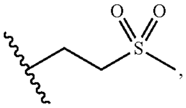,

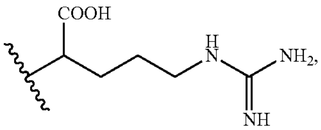

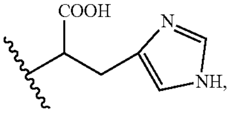 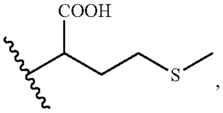,

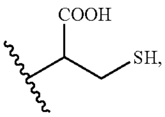 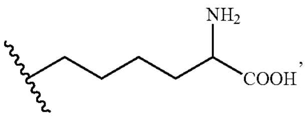, and

-continued

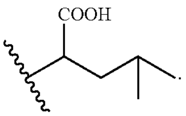.

Preferably, additional conjugates are selected from the group consisting of conjugates of the following formula (2)

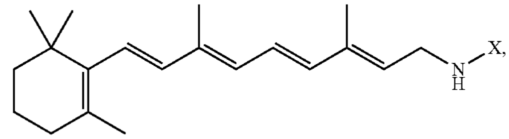

conjugates of the following formula (3)

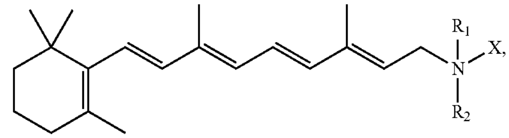

and combinations of thereof, wherein X is selected from the group consisting of

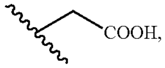 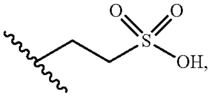

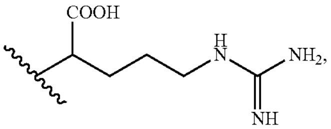

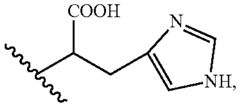 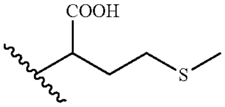,

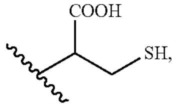 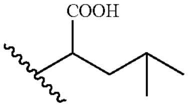,

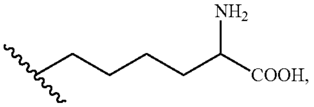 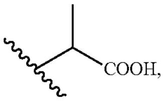

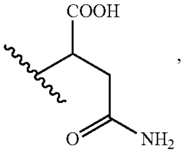, 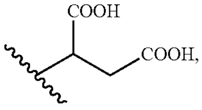

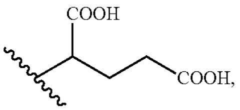 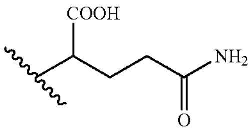,

-continued

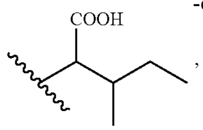,
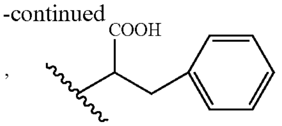,
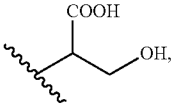
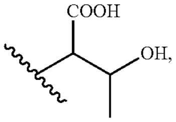
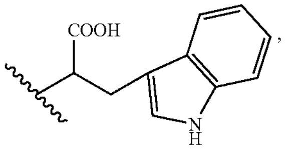
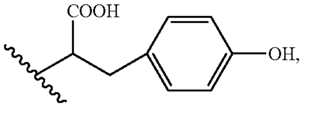
and
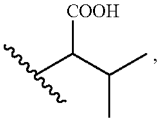

and wherein $R_1$ and $R_2$ are independently selected from the group consisting of —H, —$CH_3$, —$CH_2CH_3$, and —$CH_2CH_2$—(O—$CH_2CH_2)_m R_3$, wherein m is in a range of from 1 to 20, for example from 1 to 5, and wherein $R_3$ is selected from the group consisting of —H, —OH, —$NH_2$, —SH, —COOH, and —$OCH_3$. Preferably, X is selected from the group consisting of

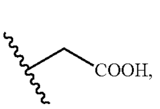
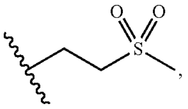
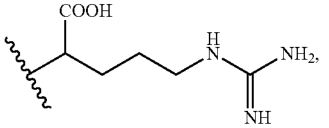
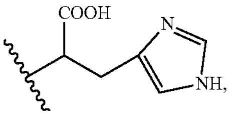
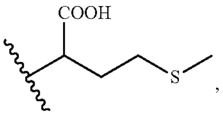
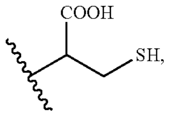
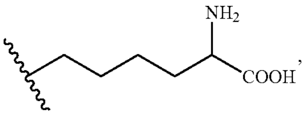
and
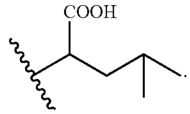

Preferably, the total molar amount of conjugates of formula (1), (2), (3), (4), (5) and (6) is at least 50 Mol %, more preferred at least 60 Mol %, more preferred at least 70 Mol %, more preferred at least 80 Mol %, more preferred at least 90 Mol %, more preferred at least 95 Mol %, more preferred at least 98 Mol %, more preferred at least 99 Mol %, more preferred at least 99.9 Mol %, most preferred 100 Mol % as compared to the total molar amount of conjugates constituting the nano-assembly. Most preferably, the nano-assemblies of the invention are essentially not formed by conjugates other than conjugates of formulas (1), (2), (3), (4), (5) and (6).

The following scheme shows preparation of a particular preferred conjugate of formula (2), i.e. a conjugate of retinal and glycine conjugate via an amine linkage.

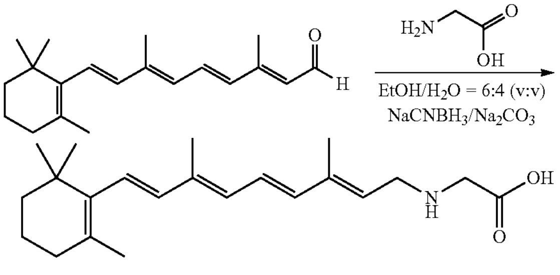

The following scheme shows preparation of a particular preferred conjugate of formula (2), i.e. a conjugate of retinal and taurine conjugate via an amine linkage.

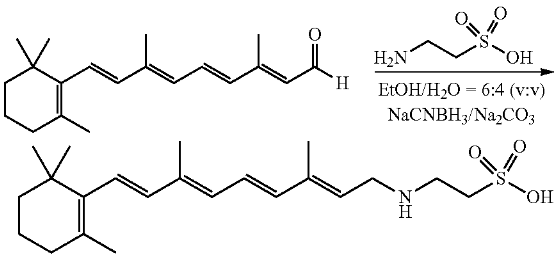

The amino acid moiety preferably comprises at least one charged group and/or at least one polar group. The amino acid is preferably water-soluble, in particular having a water-solubility of at least 300 microgram per milliliter or at least 400 microgram per milliliter water at 20° C.

Preferably, the amino acid is selected from the group consisting of taurine, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, polyethylene glycol, and combinations of two or more thereof.

The general formula (1) of the conjugate is as below

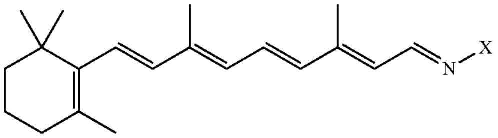

wherein X is selected from the group consisting of

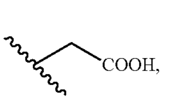
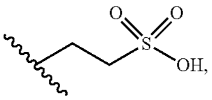
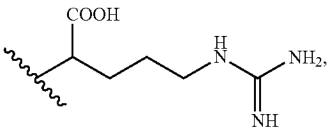

-continued
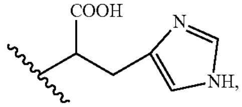
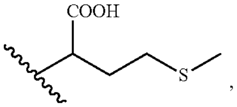
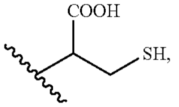
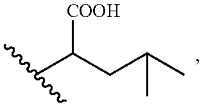
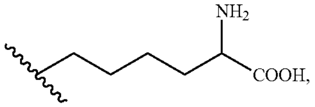
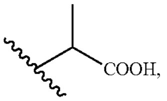
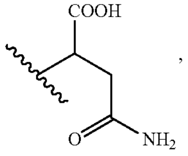
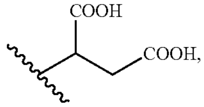
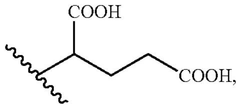
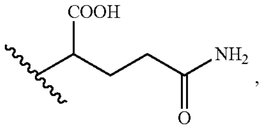
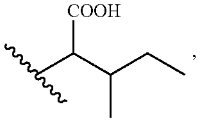
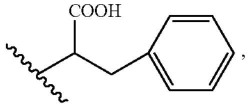
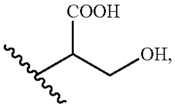
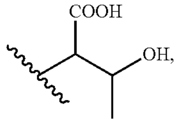
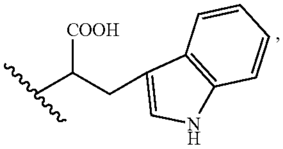
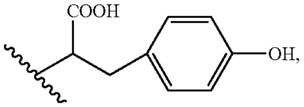
and
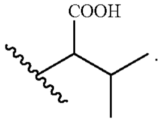
Preferably, X is selected from the group consisting of
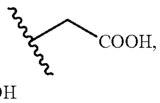
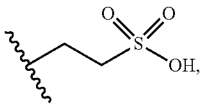
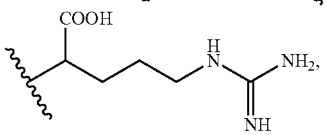
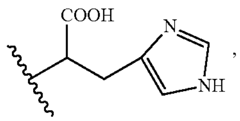
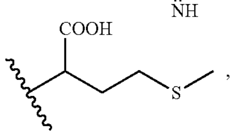
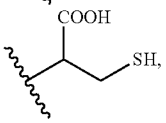
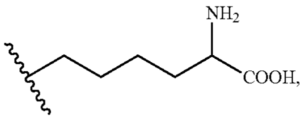
and
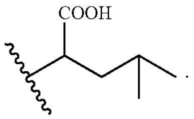
Preferably, the nano-assembly comprises conjugates of formula (1) selected from the group consisting of
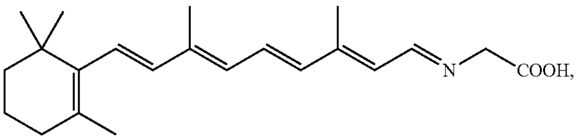
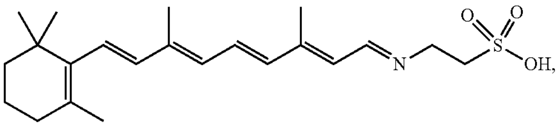
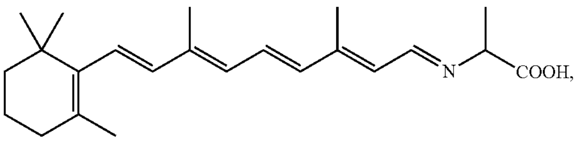
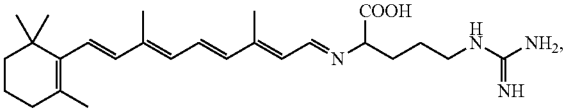
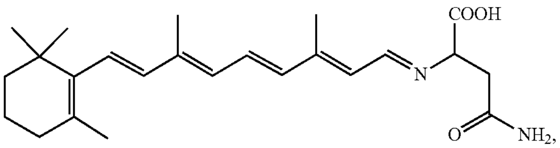
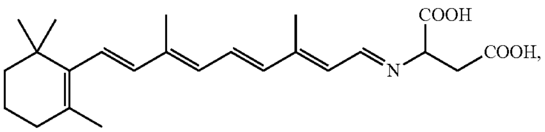
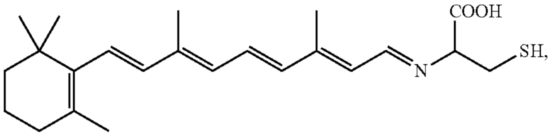
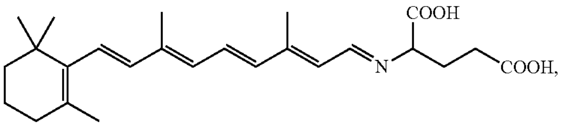
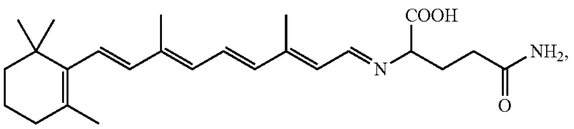
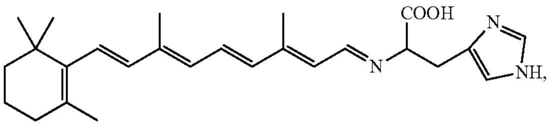
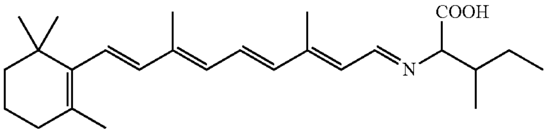
,
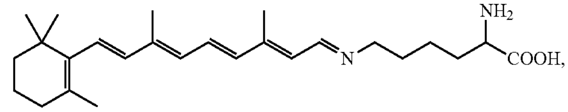

-continued
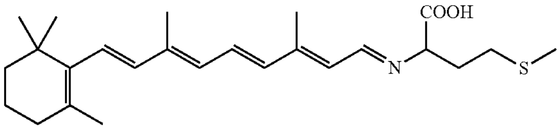
,
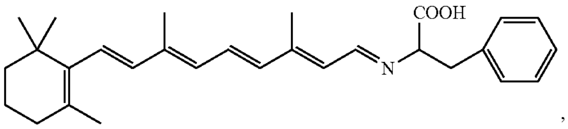
,
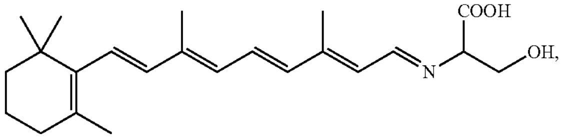
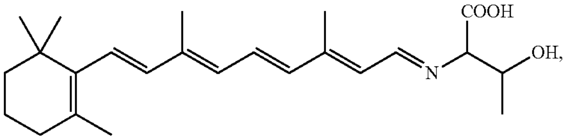
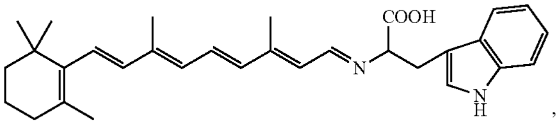
,
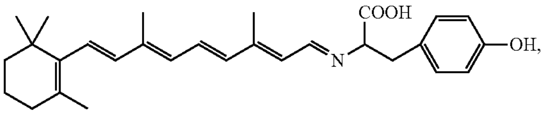
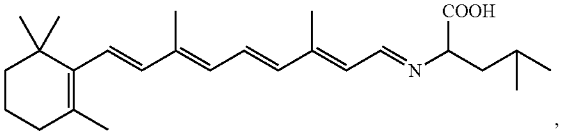
,
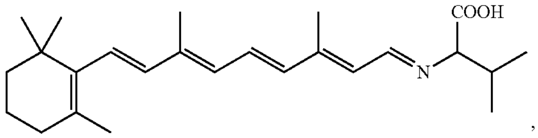
,
and combinations of two or more thereof.
Additional conjugates of formula (2) are preferably selected from the group consisting of
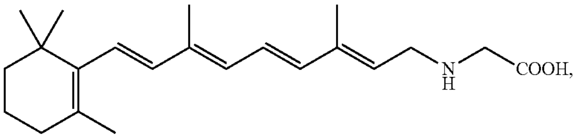
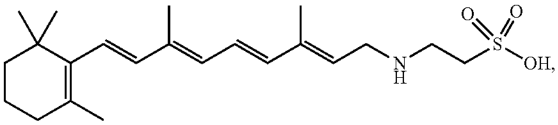
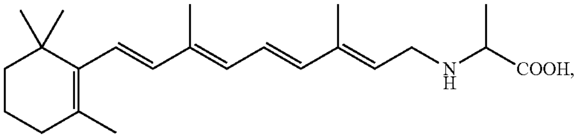
-continued
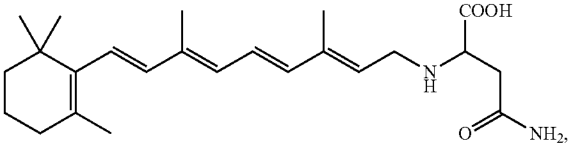
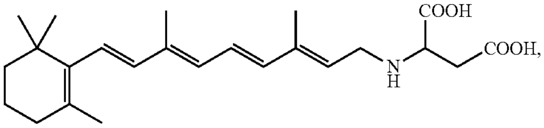
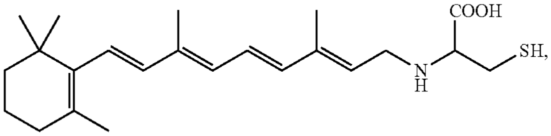
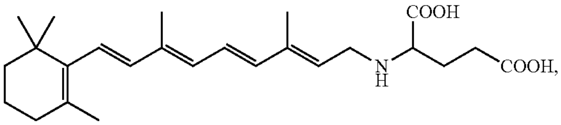
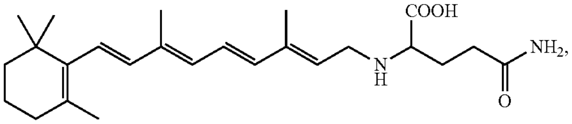
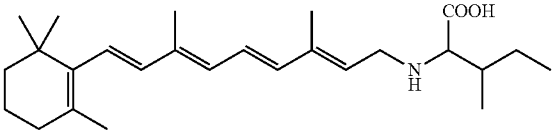
,
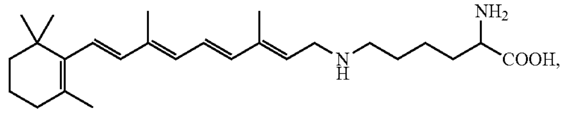
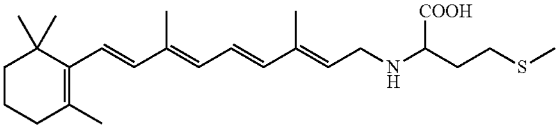
,
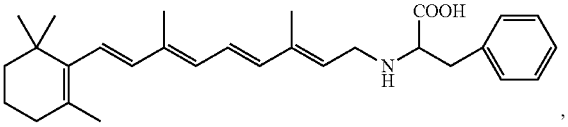
,
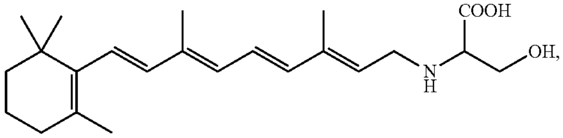
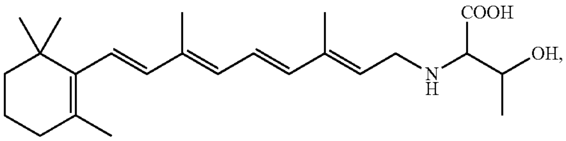
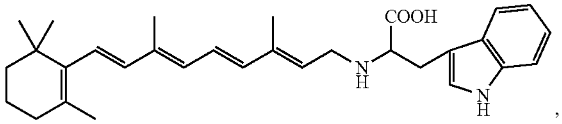
,
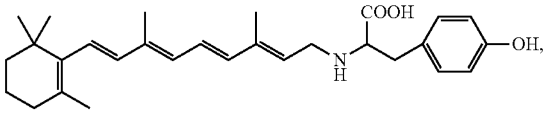

-continued

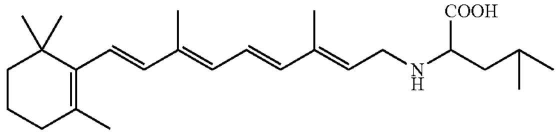

,

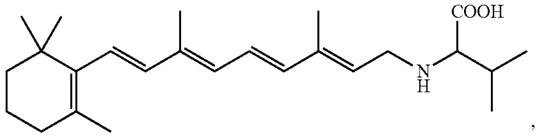

, and combinations of two or more thereof.

Additional conjugates of formula (3) are preferably selected from the group consisting of

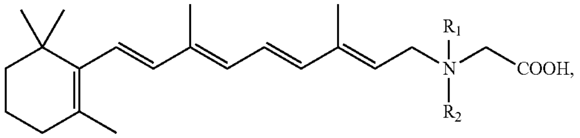

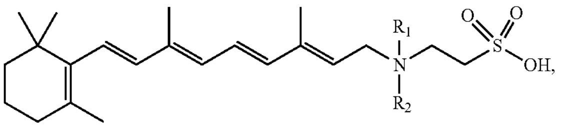

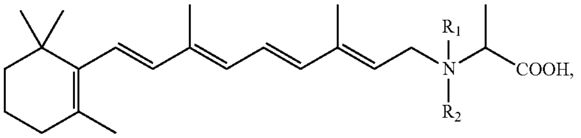

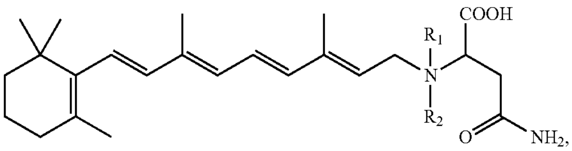

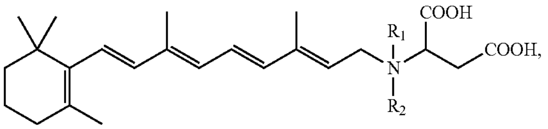

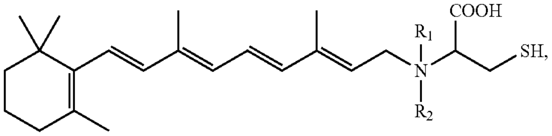

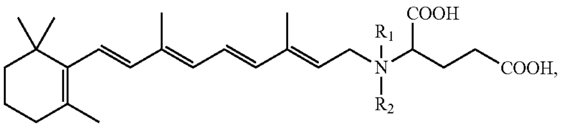

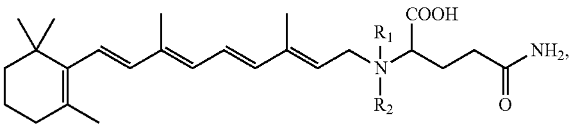

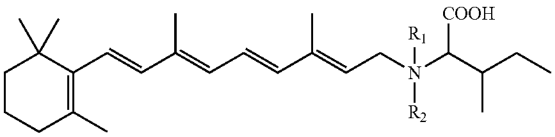

,

-continued

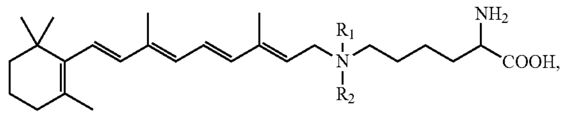

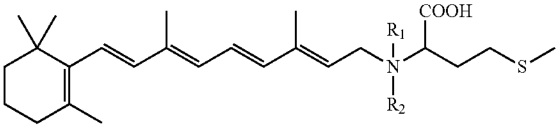

,

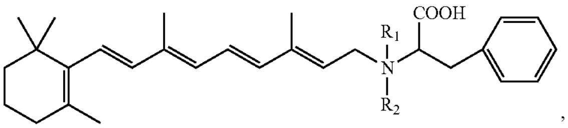

,

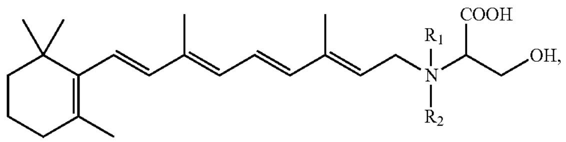

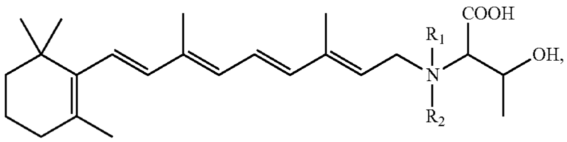

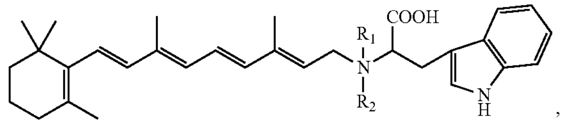

,

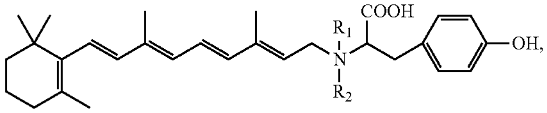

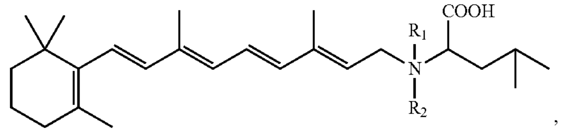

,

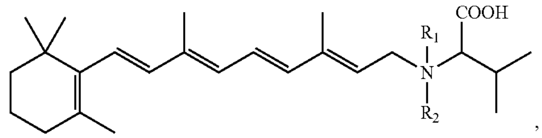

, and combinations of two or more thereof, wherein $R_1$ and $R_2$ are independently selected from the group consisting of —H, —$CH_3$, —$CH_2CH_3$, and —$CH_2CH_2$—(O—$CH_2CH_2)_m$—$R_3$, wherein m is in a range of from 1 to 20, for example from 1 to 5, and wherein $R_3$ is selected from the group consisting of —H, —OH, —$NH_2$, —SH, —COOH, and —$OCH_3$.

In embodiments of the invention, the nano-assembly comprises conjugates of the following formula (4)

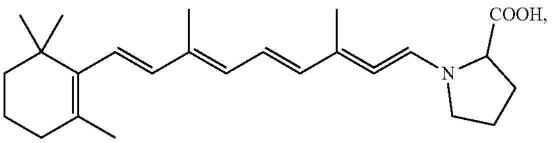 [SMILES: CC(=C=CN1CCCC1C(=O)O)/C=C/C=C(C)/C=C/C1=C(C)CCCC1(C)C]

conjugates of the following formula (5)

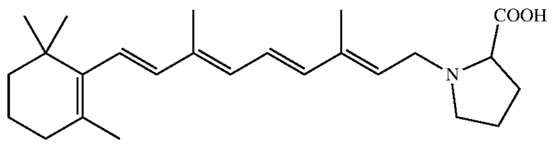 [SMILES: CC1=C(/C=C/C(C)=C/C=C/C(C)=C/CN2CCCC2C(=O)O)C(C)(C)CCC1]

and/or conjugates of the following formula (6)

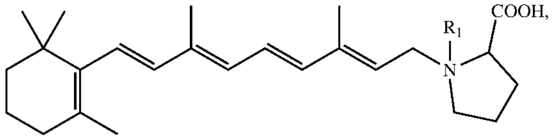

wherein $R_1$ is selected from the group consisting of —H, —$CH_3$, —$CH_2CH_3$, and —$CH_2CH_2$—(O—$CH_2CH_2)_m$—$R_3$, wherein m is in a range of from 1 to 20, for example from 1 to 5, and wherein $R_3$ is selected from the group consisting of —H, —OH, —$NH_2$, —SH, —COOH, and —$OCH_3$.

The conjugate of formula (4) has an enamine linkage and is thus pH-sensitive in contrast to the conjugates of formula (5) and formula (6).

The nano-assembly of the invention may further comprise at least one additional retinoid compound, one additional vitamin E compound, one additional vitamin D compound, and/or one additional vitamin K compound bound to the nano-assembly by non-covalent interactions. In particular, additional retinoid compounds, additional vitamin E compounds, additional vitamin D compounds, and/or additional vitamin K compounds may be loaded into the nano-assemblies of the invention by hydrophobic interaction. Vitamin E compounds are referred to as alpha-tocotrienol, beta-tocotrienol, gamma-tocotrienol, delta-tocotrienol, alpha-tocopherol, beta-tocopherol, gamma-tocopherol, delta-tocopherol and chemically related compounds. Vitamin D compounds are referred to as vitamin D1, vitamin D2, vitamin D3, vitamin D4, vitamin D5 and chemically related compounds. Vitamin D1 is also referred to as mixture of ergocalciferol and lumisterol. Vitamin D2 is also referred to as ergocalciferol. Vitamin D3 is also referred to as cholecalciferol. Vitamin D4 is also referred to as 22-dihydroergocalciferol. Vitamin D5 is also referred to as sitocalciferol. Vitamin K compounds are referred to as vitamin K1, vitamin K2 and chemically related compounds. Preferably, additional retinoid compounds, additional vitamin E compounds, and/or additional vitamin D compounds are loaded into the nano-assemblies of the invention. More preferably, additional retinoid compounds are loaded into the nano-assemblies of the invention. Preferably, the additional retinoid compound is retinol and retinol esters (or retinyl esters), retinoic acid, isotretinoin, alitretinoin or chemically related compounds. More preferably, the additional retinoid compound is retinol, retinal, retinoic acid, isotretinoin, alitretinoin, etretinate, acitretin, adapalene, bexarotene, tazarotene, or trifarotene. More preferably, the additional retinoid compound is retinol, retinal, isotretinoin, alitretinoin, or all-trans retinoic acid. More preferably, the additional retinoid compound is all-trans retinoic acid.

The term "loading weight percentage" of a nano-assembly as used herein refers to the total mass of retinoid compounds and retinoid moiety of a nano-assembly divided by the total mass of the respective nano-assembly. The loading weight percentage of retinoid compounds and retinoid moiety in the formulation is calculated by the equation (I).

$$\text{Loading weight percentage of retinoids} = \frac{\text{Mass of retinoids in the formulation}}{\text{Total mass of the formulation}} \times 100 \qquad \text{(I)}$$

whereas total mass of the formulation is sum of mass of retinoids in the formulation and mass of excipients used in the formulation, mass of retinoids is sum of mass of retinoid compounds and mass of retinoid moiety.

For example, a nano-assembly consisting of conjugates of the following formula

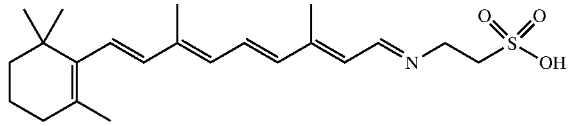 [SMILES: CC1=C(/C=C/C(C)=C/C=C/C(C)=C/C=N/CCS(=O)(=O)O)C(C)(C)CCC1]

has a retinoid moiety loading weight percentage of 68.2%, while a nano-assembly consisting of conjugates of the following formula

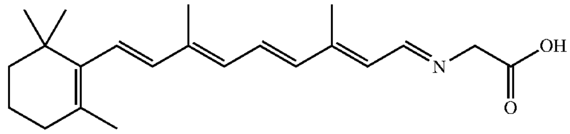 [SMILES: CC1=C(/C=C/C(C)=C/C=C/C(C)=C/C=N/CC(=O)O)C(C)(C)CCC1]

has a retinoid moiety loading weight percentage of 78.3%.

Nano-assemblies that have not been loaded with additional retinoid compound, have a loading weight that is entirely determined by the conjugates that the nano-assembly is consisting of. In particular, the proportion of the mass of the retinoid moiety of the conjugates as compared to the overall mass of the conjugates determines the loading weight of such nano-assemblies. Due to the respective conjugates, the nano-assemblies of the invention have a particular high loading weight. Notably, the loading weight can be increased by using amino acids having a comparably low molecular weight, for example taurine or glycine.

Moreover, as described above, the nano-assembly of the invention may further comprise at least one additional retinoid compound bound to the nano-assembly by non-covalent interactions. In particular, the loading weight percentage of the nano-assemblies can be further increased by loading additional retinoid compounds into the nano-assemblies.

The loading weight percentage of the nano-assemblies is preferably in a range of from 5% to 90%. More preferably, the loading weight percentage of the nano-assemblies is in a range from 15% to 80%. It is a particular advantage of the invention that it can provide such tunable and high loading weight percentages. Preferably, the loading weight percentage of the nano-assemblies is at least 5%, at least 10%, at least 15%, at least 20%, at least 30%, at least 40%, or at least 50%. The loading weight percentage may for example be at most 90% or at most 80%.

Nano-assemblies consisting of the conjugates of formula (1) and/or formula (4) are considered as excipient-free nano-assemblies, which allow 100% loading weight percentage of compounds, retinoids and amino acids, having therapeutic benefits.

The present invention also relates to an aqueous composition comprising the nano-assembly of the invention. For example, the hydrodynamic diameter of the nano-assembly may be in a range of from 30 nm to 1000 nm, particularly from 100 nm to 950 nm or from 200 nm to 900 nm. The hydrodynamic diameter of the nano-assembly may for example be at least 30 nm, at least 100 nm or at least 200 nm. The hydrodynamic diameter of the nano-assembly may for example be at most 1000 nm, at most 950 nm or at most 900 nm. The hydrodynamic diameter as used herein preferably refers to the average hydrodynamic diameter of the nano-assemblies.

The polydispersity index PDI may for example be in a range of from 0.01 to 0.3, particularly from 0.02 to 0.25 or from 0.05 to 0.2.

The PDI is calculated based on the standard deviation s and the mean m of the hydrodynamic diameter d of the nano-assemblies measured using dynamic light scattering (DLS, NanoBrook, Brookhaven Instruments, Holtsville, NY; the device is equipped with a 40 mW diode laser scattering angle of 90° at 25° C.) according to the following formula.

$$PDI = \left(\frac{s(d)}{m(d)}\right)^2$$

In the respective formula, the term s(d) refers to the standard deviation of the diameter of the nano-assemblies. The term m(d) refers to the mean of the diameter of the nano-assemblies. The PDI is preferably at most 0.3, more preferably at most 0.25, more preferably at most 0.2. A low PDI is associated with high homogeneity. The PDI may be at least 0.001, at least 0.01, at least 0.02 or at least 0.05.

The zeta-potential may, for example, be in a range of from −50 mV to +50 mV, particularly from −45 mV to +40 mV or from −40 mV to +10 mV. It is a particular advantage of the invention that it can provide such tunable zeta-potential values. The zeta-potential is advantageous for maintaining the long-term stability of the nano-assemblies. The zeta-potential of the nano-assemblies dispersed in water, phosphate-buffered saline (1×) or in sodium chloride (10 mM) aqueous solution is measured using dynamic light scattering (DLS, NanoBrook, Brookhaven Instruments, Holtsville, NY; the device is equipped with a 40 mW diode laser scattering angle of 90° at 25° C.). The zeta-potential may for example be at least −50 mV, at least −45 mV or at least −40 mV. The zeta-potential may for example be at most +50 mV, at most +40 mV or at most +10 mV.

The nano-assemblies of the present invention may be characterized by a particular high storage stability, in particular regarding the hydrodynamic diameter and/or the PDI. For example, the hydrodynamic diameter of the nano-assemblies at a time point of 3 hours after preparation of the nano-assemblies may differ from the hydrodynamic diameter of the nano-assemblies after storage for 7 days, 15 days, 21 days or 28 days by at most 80 nm, at most 70 nm, or at most 60 nm when stored in aqueous solution, for example water, at a concentration of 50 μg/ml at room temperature (25-30° C.) and ambient pressure. The PDI at a time point of 3 hours after preparation of the nano-assemblies may differ from the PDI after storage for 7 days, 15 days, 21 days or 28 days by at most 0.15, at most 0.12, at most 0.10, at most 0.08, or at most 0.07 when stored in aqueous solution, for example water, at a concentration of 50 μg/ml at room temperature (25-30° C.) and ambient pressure.

The present invention also relates to a pharmaceutical composition comprising the nano-assembly of the invention. The pharmaceutical composition may include sodium, potassium, calcium, magnesium, chloride, sulfate, hydroxide, hydrogen carbonate, and/or carbonate ions. The pharmaceutical composition may also include polyethylene glycol, hyaluronic acid, sodium hyaluronate, collagen, hydroxyethylcellulose, xanthan gum, acacia gum, glucomannan, sclerotium gum, polyacrylamide, dimethiconols, dimethicone crosspolymer, dimethicone/vinyl dimethicone crosspolymer, polyquaternium-6, polyquaternium-7, and/or polyquaternium-11. The pharmaceutical composition may be an aqueous suspension of the nano-assemblies. The pH of the pharmaceutical composition may for example be in a range of from 6.5 to 7.4, particularly from 6.65 to 7.2 or from 6.8 to 7.0. The pH of the pharmaceutical composition may for example be at least 6.5, at least 6.65 or at least 6.8. The pH of the pharmaceutical composition may for example be at most 7.4, at most 7.2 or at most 7.0.

The present invention also relates to the nano-assembly and/or the pharmaceutical composition of the invention for use in medicine.

The present invention also relates to the nano-assembly and/or the pharmaceutical composition of the invention for use as a medicament.

The present invention also relates to the nano-assembly of the invention for use in the treatment of pulmonary diseases and/or dermatological diseases.

Pulmonary diseases are diseases of the lung. The invention relates for example to nano-assemblies for use in the treatment of bronchopulmonary dysplasia, in particular in premature infants. The invention also relates to nano-assemblies for the treatment of pulmonary infections, asthmatic diseases and/or chronic obstructive pulmonary disease (COPD), in particular in adults.

Dermatological diseases are diseases of the skin. The invention relates to nano-assemblies for treatment of chronic and severe acne, acne conglobate, psoriasis (including plaque psoriasis, pustular psoriasis, napkin psoriasis, guttate psoriasis, erythrodermic psoriasis, seborrheic-like psoriasis, and psoriatic arthritis), photoaging, skin cancer, actinic keratosis, pre-neoplasm disorders, initial neoplasm, multiple neoplasms, ichthyosis, melasma, and lichen planus, HIV-associated Kaposi sarcoma, genodermatosis (ichthyosis), pitiriasis rubra pilaris, hypertrophic scar, rosacea, chronic hyperkeratosis, mucosal keratinization, neoplasms (e.g. Lymphoma of the skin), wound healing, skin pigmentation disorders, stretch marks on the skin, viral infections, xerophthalmia; actinic keratosis, oral leukoplakia, xeroderma pigmentosum, nevoid basal-cell carcinoma, basal-cell carcinoma, Darier's disease, confluent and reticulated papillomatosis, atrophoderma vermiculatum, ulerythema ophryogenes, palmoplantar keratoderma, Papillon-Lefèvre syndrome, Vohwinkel syndrome, acanthosis nigricans, Muir-Torre syndrome, Cowden's disease, cutaneous T cell lymphoma, histiocytosis of Langerhans cells, oral leukoplakia, Bowen's disease, queyrat erythroplasia, metastatic melanoma, skin cancer in transplanted patients, cutaneous sarcoidosis, granuloma annulare, O'brien's actinic granuloma, siliconoma, Rosacea, rosacea fulminans, solid cutaneous edema, rhinophyma, cutaneous disseminated lupus, cystic acne, steatocystoma multiplex, hidradenitis suppurativa, ofuji's syndrome, multiple syringomas, actinic folliculitis, sclerosing folliculitis of the neck, keratosis pilaris, folliculitis decalvans, folliculitis by pityrosporum, folliculitis by Gram negative, recurrent folliculitis, genital wart, scleroderma, alopecia mucinosa, discoid lupus erythematosus, systemic scleroderma, chronic lichenoid keratosis, lichen-like diseases, infectious diseases, and/or pyogenic granuloma.

The invention also relates to a method of treatment of pulmonary diseases and/or dermatological diseases, in particular treatment of bronchopulmonary dysplasia, in particular in premature infants, treatment of pulmonary infections, asthmatic diseases and/or chronic obstructive pulmonary disease (COPD), in particular in adults, and/or treatment of chronic and severe acne, acne conglobate, psoriasis (including plaque psoriasis, pustular psoriasis, napkin psoriasis, guttate psoriasis, erythrodermic psoriasis, seborrheic-like psoriasis, and psoriatic arthritis), photoaging, skin cancer, actinic keratosis, pre-neoplasm disorders, initial neoplasm, multiple neoplasms, ichthyosis, melasma, and lichen planus, HIV-associated Kaposi sarcoma, genodermatosis (ichthyosis), pitiriasis rubra pilaris, hypertrophic scar, rosacea, chronic hyperkeratosis, mucosal keratinization, neoplasms (e.g. Lymphoma of the skin), wound healing, skin pigmentation disorders, stretch marks on the skin, viral infections, xerophthalmia; actinic keratosis, oral leukoplakia, xeroderma pigmentosum, nevoid basal-cell carcinoma, basal-cell carcinoma, Darier's disease, confluent and reticulated papillomatosis, atrophoderma vermiculatum, ulerythema ophryogenes, palmoplantar keratoderma, Papillon-Lefèvre syndrome, Vohwinkel syndrome, acanthosis nigricans, Muir-Torre syndrome, Cowden's disease, cutaneous T cell lymphoma, histiocytosis of Langerhans cells, oral leukoplakia, Bowen's disease, queyrat erythroplasia, metastatic melanoma, skin cancer in transplanted patients, cutaneous sarcoidosis, granuloma annulare, O'brien's actinic granuloma, siliconoma, Rosacea, rosacea fulminans, solid cutaneous edema, rhinophyma, cutaneous disseminated lupus, cystic acne, steatocystoma multiplex, hidradenitis suppurativa, ofuji's syndrome, multiple syringomas, actinic folliculitis, sclerosing folliculitis of the neck, keratosis pilaris, folliculitis decalvans, folliculitis by pityrosporum, folliculitis by Gram negative, recurrent folliculitis, genital wart, scleroderma, alopecia mucinosa, discoid lupus erythematosus, systemic scleroderma, chronic lichenoid keratosis, lichen-like diseases, infectious diseases, and/or pyogenic granuloma.

The present invention also relates to the non-medical use of the nano-assembly of the invention for management and elimination of stretch marks on the skin (striae), treatment of androgenetic alopecia, management of smooth wrinkles and fine lines, and anti-ageing.

The present invention also relates to the method of synthesizing the conjugates of the invention, the method comprising the step of mixing a retinoid compound (in particular all trans retinal) and an amino acid, in particular at a molar ratio of 1:50 to 1:1, in a mixture of a polar solvent A and a polar solvent B. The molar ratio of retinoid compound to amino acid may for example be at most 1:1, at most 1:2, or at most 1:5. The molar ratio of retinoid compound to amino acid may for example be at least 1:50, at least 1:25, or at least 1:10.

The polar solvent A is preferably water or water supplemented with sodium, potassium, calcium, magnesium, chloride, sulfate, hydroxide, hydrogen carbonate, and/or carbonate ions. Notably, water may also be supplemented with polyethylene glycol, hyaluronic acid, sodium hyaluronate, collagen, hydroxyethylcellulose, xanthan gum, acacia gum, glucomannan, sclerotium gum, polyacrylamide, dimethiconols, dimethicone crosspolymer, dimethicone/vinyl dimethicone crosspolymer, polyquaternium-6, polyquaternium-7, and/or polyquaternium-11. The solvent A may have pH values in a range of 6.5 to 7.4, particularly from 6.65 to 7.2 or from 6.8 to 7.0. The solvent A is preferably an aqueous solution.

The polarity of solvents A and B can be described by the polarity index. In the present specification, it is referred to the polarity index, according to Paul C. Sadek, The HPLC Solvent Guide, 2nd Edition, Wiley-Interscience, 2002. Higher values of the polarity index indicate a higher polarity of the solvent. For example, water has a polarity index of 9.0. Preferably, the polarity index of solvent A is at least 8.0, more preferably at least 8.5, and/or at most 9.0, more preferably at most 8.75. Preferably, the polarity index of solvent A is in a range from 8.0 to 9.0, for example from 8.5 to 8.75. Preferably, the polarity index of solvent A is about 9.0. The polarity index of solvent A is preferably higher as compared to the polarity index of solvent B.

Preferably, solvent B has a polarity index of from 3.0 to 7.5, more preferably of from 3.5 to 6.5, more preferably from 3.9 to 6.0. Preferably, solvent B is selected from the group consisting of ethanol, acetone, tetrahydrofuran (THF), acetonitrile, methanol, isopropyl alcohol, dioxane, dimethylformamide (DMF) and dimethylsulfoxide (DMSO). More preferably, solvent B is selected from the group consisting of ethanol, acetone, THF, acetonitrile, methanol, isopropyl alcohol and dioxane. More preferably, solvent B is selected from the group consisting of ethanol, acetone, THF and isopropyl alcohol. More preferably, solvent B is ethanol.

The solvent A and the solvent B are preferably mixed at the volume ratio in a range from 1:50 to 1:1.

Incubating the mixture of the retinoid and the amino acid in the mixture of a polar solvent A and a polar solvent B at room temperature for a time of from 1 h to 48 h is particularly advantageous for forming imine or enamine linkage.

The present invention also relates to a method of producing the nano-assembly of the invention, the method comprising the step of providing a mixture of a retinoid compound and an amino acid at a molar ratio from 1:50 to 1:1, in a mixture of a polar solvent A and a polar solvent B. The solvent A and the solvent B are mixed at the volume ratio from 1:50 to 1:1. Notably, conjugates of formula (1) are formed in the mixture. Furthermore, the conjugates form nano-assemblies spontaneously in solvent A upon removal of solvent B.

The method may further comprise the step of isolating the conjugate. For example, following the removal of solvent B, the conjugate may be extracted with an excess amount of chloroform and dried over magnesium sulfate ($MgSO_4$). Chloroform may then be removed, for example under reduced pressure at room temperature, and the residue solvent may then be dried under, for example at reduced pressure at room temperature for 12 h. The conjugate may then be dissolved in a mixture of solvents A and B. The nano-assemblies can be formed spontaneously in water upon removal of solvent B.

The method of the invention is particularly advantageous due to its high isolated yield. Preferably, the isolated yield is higher than 50%, higher than 75%, higher than 80%, higher than 85%, higher than 90%, or higher than 95%. In some embodiments, the isolated yield may be at most 99.9%, at most 99%, or at most 98%. The isolated yield is calculated as the ratio of the molar amount of isolated conjugate that was obtained to the molar amount of the retinoid compound used for making the conjugate. For example, if 1 mol of all-trans retinal and 1 mol of taurine were used as reactants and 0.9 mol of conjugate were obtained, the isolated yield is 90%. Likewise, if 1 mol of all-trans retinal and 2 mol of taurine were used as reactants and 0.9 mol of conjugate were obtained, the isolated yield is 90%. If the retinoid compound is used in molar excess over the amino acid, the isolated yield has to be calculated as the ratio of the molar amount of isolated conjugate that was obtained to the molar amount of the amino acid used for making the conjugate. However, it is generally preferred that the molar ratio of retinoid compound to amino acid is in a range of from 1:1 to 1:50 so that the retinoid compound is normally not used in molar excess over the amino acid.

Particularly preferred methods of producing the nano-assemblies of the invention are shown in the following schemes.

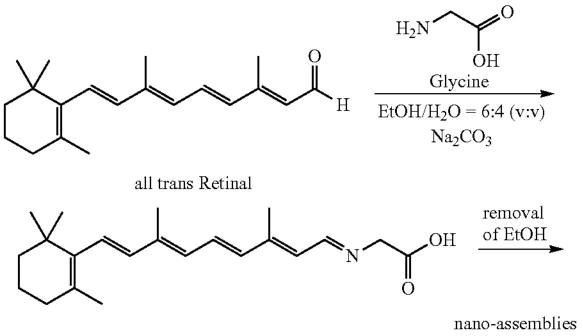

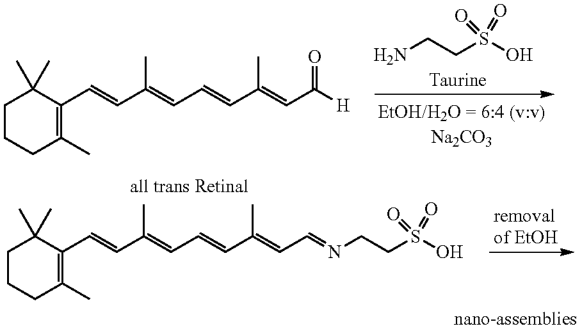

If a pH-sensitive imine or enamine linkage is not desired (as for producing conjugates of formulas (2), (3), (5) and/or (6)), it is possible to add reducing agents to the mixture of the retinoid compound and the amino acid in the solvent A during the synthetic step. This enables reducing the imine or enamine group, in particular, such that an amine group is obtained. Particularly, preferred reducing agents are selected from the group consisting of borohydrides and cyanoborohydrides. Cyanoborohydrides are particularly preferred, in particular sodium cyanoborohydride ($NaCNBH_3$). The borohydrides or cyanoborohydrides are preferably removed completely by extraction or membrane dialysis method prior to the nano-assemblies preparation. The following schemes show exemplarily a method of the invention for producing nano-assemblies comprising conjugates of formula (2) not including a pH-sensitive linking group.

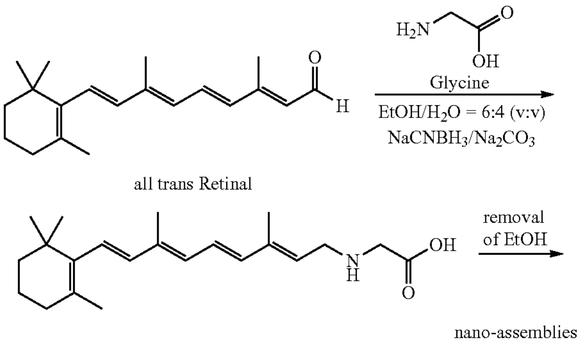

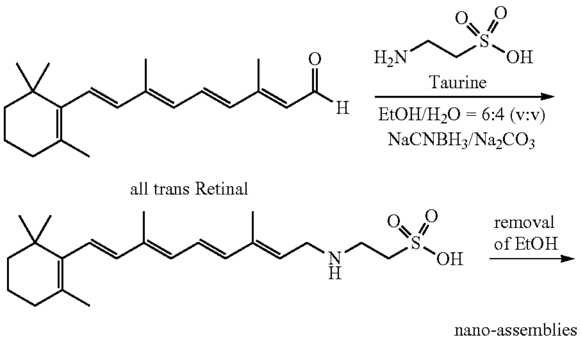

The method may further comprise the step of adding at least one additional retinoid compound, at least one additional vitamin E compound, at least one additional vitamin D compound, and/or at least one additional vitamin K compound to the mixture of the retinoid compound and the amino acid in the solvent B. Preferably, an additional retinoid compound is added. Particularly preferred, the additional retinoid compound is retinoic acid, in particular all trans retinoic acid (ATRA). The following schemes show exemplarily production of preferred ATRA-loaded nano-assemblies of the invention.

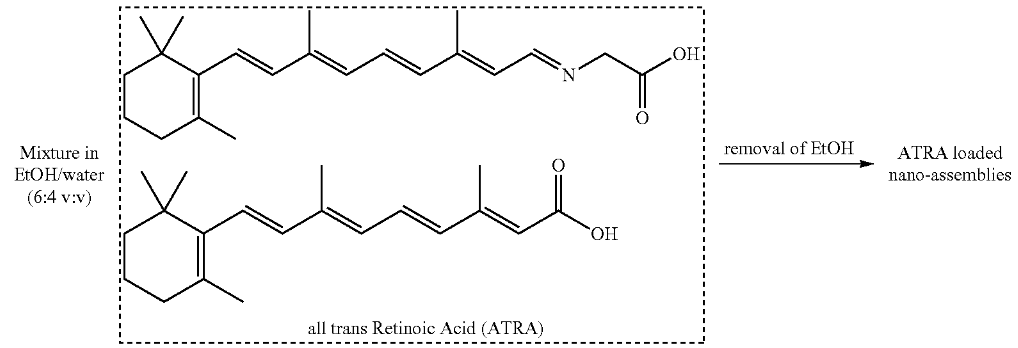

-continued

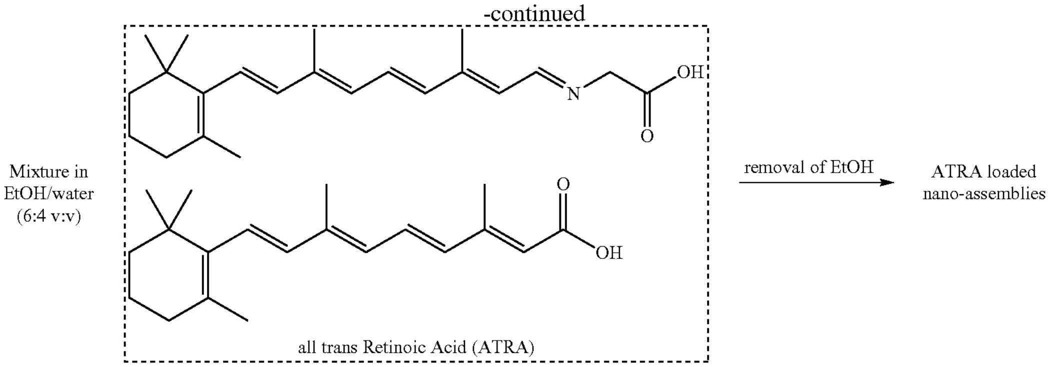

all trans Retinoic Acid (ATRA)

EXAMPLES

Figure 1:
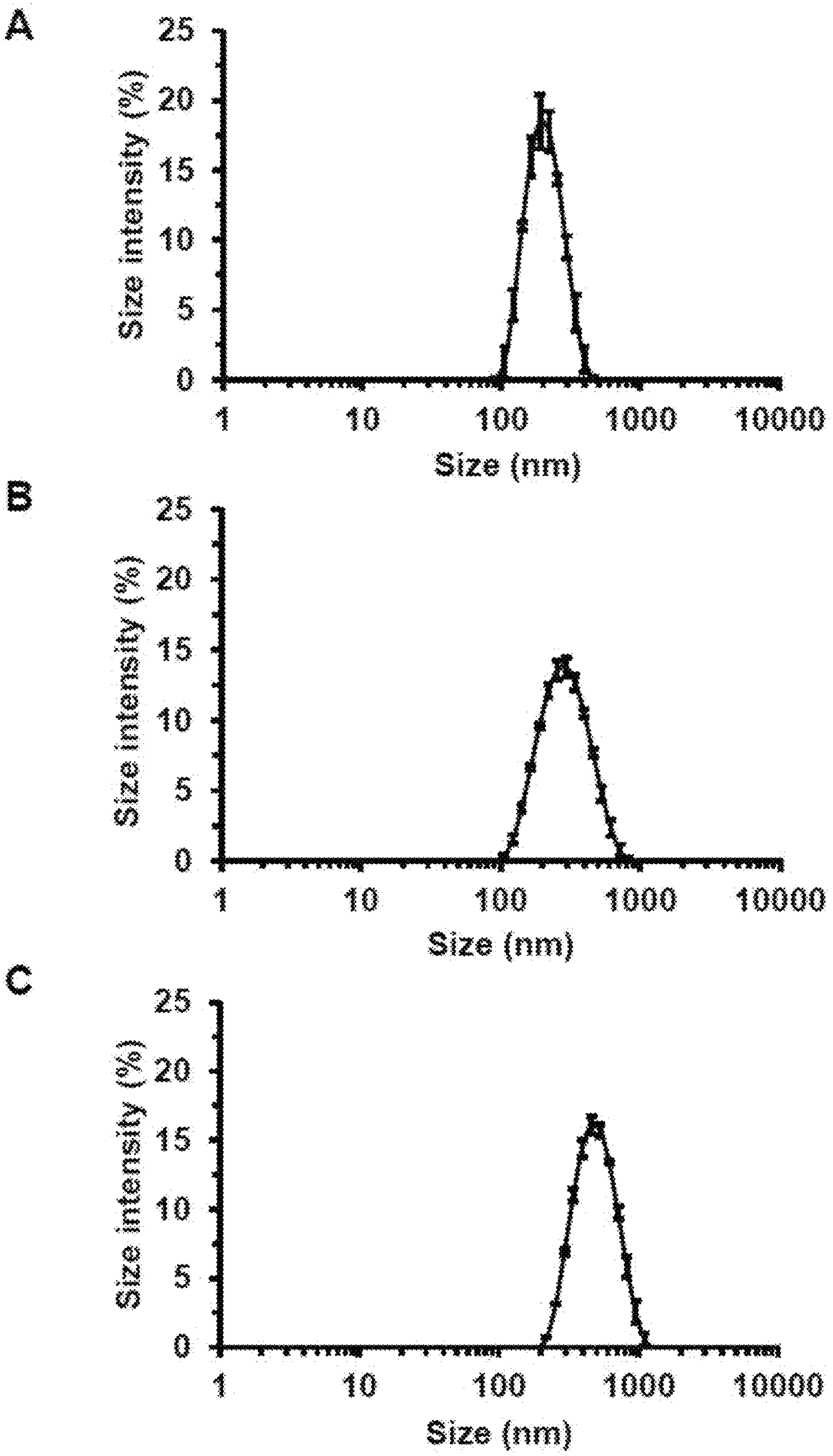
FIG. 1 shows the size distribution of different nano-assemblies of the invention. The hydrodynamic diameter (in nm) is shown on the x-axis on logarithmic scale. The size intensity (in percent) is shown on the y-axis. The size distribution was obtained using dynamic light scattering (DLS). The curves shown in FIGS. 1A, 1B and 1C correspond to the nano-assemblies made at a concentration of 0.5, 1 and 2 mg/mL (w/w), respectively.

The invention is further explained based on the following examples.

1. Nano-Assemblies Based on Conjugates of All Trans Retinal and Glycine

All trans retinal and glycine were mixed in polar solvent consisting of ethanol (EtOH) and water. The molar ratio of retinal to glycine was 1:1.1. The volume ratio of EtOH to $H_2O$ was 6:4 (v/v). Sodium carbonate was added to the mixed solution at a molar ratio of retinal to sodium carbonate of 1:10. The reaction was carried out at room temperature for 24 h.

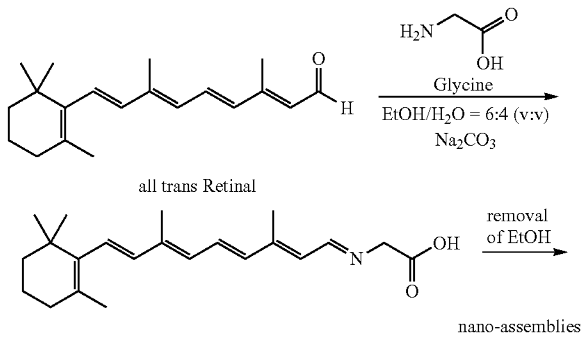

all trans Retinal

The nano-assemblies were formed spontaneously in water upon removal of EtOH.

The conjugate can be isolated using the following procedure. Following the removal of EtOH, the conjugate is extracted with an excess amount of chloroform and dried over magnesium sulfate ($MgSO_4$). Chloroform is then removed under reduced pressure at room temperature, and the residue solvent is then dried under reduced pressure at room temperature for 12 h. The conversion yield was 100%, while the isolated yield was higher than 95%. The conjugate can be then dissolved in polar solvent consisting of ethanol (EtOH) and water. The volume ratio of EtOH to $H_2O$ was 6:4 (v/v). The nano-assemblies formed spontaneously in water upon removal of EtOH.

The loading weight percentage of retinoid was 78.3%.

Hydrodynamic diameter, polydispersity index (PDI) and zeta-potential of the nano-assemblies was determined using dynamic light scattering (DLS, NanoBrook, Brookhaven Instruments, Holtsville, NY; the device is equipped with a 40 mW diode laser scattering angle of 90° at 25° C.). The results are summarized in the following table as mean±standard deviation.

| Nano-assemblies made at the concentration (mg/mL) | Size (nm) | PDI | zeta-potential (mV) |
|---|---|---|---|
| 1.0 | 290.8 ± 1.1 | 0.05 ± 0.00 | −13.8 ± 0.2 |

The low PDI shows that there was a homogeneous size distribution.

2. Nano-Assemblies Based on Conjugates of All Trans Retinal and Taurine

All trans retinal and taurine were mixed in polar solvent consisting of ethanol (EtOH) and water. The molar ratio of retinal to taurine was 1:1.1. The volume ratio of EtOH to $H_2O$ was 6:4 (v/v). Sodium carbonate was added to the mixed solution at a molar ratio of retinal to sodium carbonate of 1:10. The reaction was carried out at room temperature for 24 h.

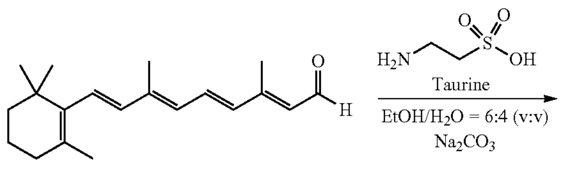

all trans Retinal

-continued

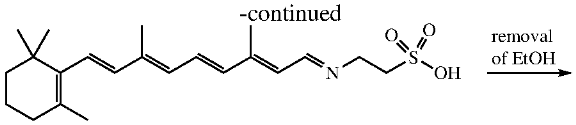

nano-assemblies

The nano-assemblies were formed spontaneously in water upon removal of EtOH.

The conjugate can be isolated using the following procedure. Following the removal of EtOH, the conjugate is extracted with an excess amount of chloroform and dried over magnesium sulfate ($MgSO_4$). Chloroform is then removed under reduced pressure at room temperature, and the residue solvent is then dried under reduced pressure at room temperature for 12 h. The isolated yield was higher than 95%. The conjugate can be then dissolved in polar solvent consisting of ethanol (EtOH) and water. The volume ratio of EtOH to $H_2O$ was 6:4 (v/v). The nano-assemblies formed spontaneously in water upon removal of EtOH.

The loading weight percentage of retinoid was 68.2%.

Hydrodynamic diameter, polydispersity index (PDI) and zeta-potential of the nano-assemblies was determined using dynamic light scattering. The results are summarized in the following table as mean±standard deviation.

| Sample | Size (nm) | PDI | zeta-potential (mV) |
|---|---|---|---|
| 1 | 203.6 ± 0.5 | 0.069 ± 0.044 | −23.0 ± 1.6 |
| 2 | 260.6 ± 0.9 | 0.144 ± 0.022 | |
| 3 | 466.4 ± 6.8 | 0.157 ± 0.015 | |

Samples 1, 2 and 3 show the characteristics of the nano-assemblies made at a concentration of 0.5, 1 and 2 mg/mL (w/w), respectively. The concentration of the nano-assemblies is referred to as the concentration in water. The concentration was varied by adding an additional amount of the polar solvent consisting of ethanol (EtOH) and water prior to the removal of EtOH.

The low PDI shows that there was a homogeneous size distribution.

The size distribution of samples 1 to 3 are shown in FIGS. 1A, 1B, and 1C, respectively.

Figure 2:
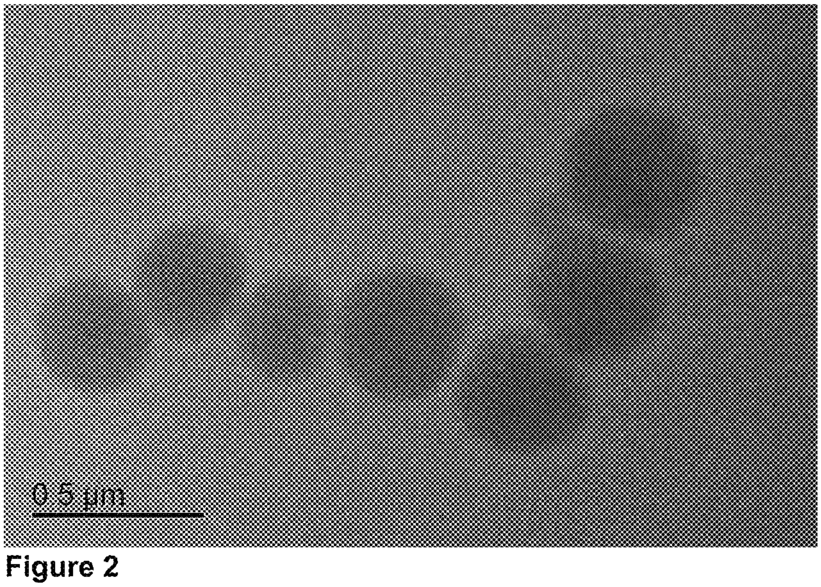
FIG. 2 is a cryogenic Transmission Electron microscopy (cryo-TEM) image of nano-assemblies of the invention dispersed in water.

A cryo-TEM image of nano-assemblies dispersed in water is shown in FIG. 2. The retinoid loading weight percentage of the nano-assemblies of FIG. 2 was 68.2%.

3. All Trans Retinoic Acid (ATRA) Loaded Nano-Assemblies Based on Conjugates of All Trans Retinal and Glycine The conjugates of all trans retinal and glycine that were synthesized and isolated in Example 1 were mixed with ATRA at the weight ratio of ATRA to the conjugates of 1:3 (w/w). The mixture was then dissolved in polar solvent consisting of ethanol (EtOH) and water. The volume ratio of EtOH to $H_2O$ was 6:4 (v/v).

The ATRA loaded nano-assemblies based on conjugates of all trans retinal and glycine were formed spontaneously in water upon removal of EtOH.

Hydrodynamic diameter, polydispersity index (PDI) and zeta-potential of the nano-assemblies was determined using dynamic light scattering (DLS, NanoBrook, Brookhaven Instruments, Holtsville, NY; the device is equipped with a 40 mW diode laser scattering angle of 90° at 25° C.). The results are summarized in the following table as mean±standard deviation.

| ATRA loaded nano-assemblies made at the concentration (mg/mL) | Size (nm) | PDI | zeta-potential (mV) |
|---|---|---|---|
| ~0.48 | 208.5 ± 3.4 | 0.08 ± 0.02 | −9.3 ± 0.5 |

The low PDI shows that there was a homogeneous size distribution.

The following table summarizes the loading weight and loading weight percentage of retinoids

| ATRA [μg/mL] | Retinal [μg/mL] | Total Retinoids [μg/mL] | Total concentration in water (including Glycine) [μg/mL] | Retinoids loading weight percentage |
|---|---|---|---|---|
| 100 | 300 | 400 | ~480 | ~83.5% |

The loading weight percentage of retinoid was about 83.5%.

This example shows that ATRA could be loaded in the nano-assemblies based on conjugates of all trans retinal and glycine using a facile method. The loading weight percentage of retinoids can be further tuned compared to Example 1 and Example 2 by adding an additional amount of ATRA.

Furthermore, the loading efficiency of ATRA was significantly high at 100%, which was analyzed by high-performance liquid chromatography (HPLC). The loading efficiency was determined as follows. The ATRA loaded nano-assemblies were completely solubilized in methanol and used in HPLC analysis. The mass of ATRA in the nano-assemblies was detected using HPLC, and the loading efficiency was determined using the following equation (II).

$$ATRA \text{ loading efficiency } (\%) = \frac{ATRA \text{ mass}_{detected}}{ATRA \text{ mass}_{beginning}} \times 100 \quad \text{(II)}$$

wherein the ATRA $\text{mass}_{detected}$ is the ATRA mass loaded in the nano-assemblies determined using HPLC, and the ATRA $\text{mass}_{beginning}$ is the initial ATRA mass used in the loading procedure.

4. pH Dependent Release Study

The nano-assemblies from Example 2 were diluted at 10% (w/v) in acetate buffer consisting of sodium acetate and acetic acid (pH 4.5, 150 mM) at 37° C. At 2 h post-incubation, the suspension was centrifuged at 15000 g for 30 min, the supernatant was removed, and the pellet was collected and freeze dried overnight. The dried compound was then dissolved in chloroform-d for proton NMR analysis.

The complete cleavage of the imine bond in the nano-assemblies was confirmed by proton NMR spectrum after 2 h incubation. In details, the corresponding proton peaks of imine bond in the conjugates typically from 8.5 ppm to 9.5 ppm disappeared, and the typical peaks of aldehyde group in retinal appeared from 9.51 ppm to 10.5 ppm. Conclusively, the complete disappearance of imine peaks confirmed the complete (100%) cleavage of the imine bond at pH 4.5 after 2 h incubation.

5. Light Stability Study

The nano-assemblies from Example 1 were diluted at 30% (w/v) in distilled water, and the solution was exposed to simulated sunlight for 2 h under the accumulated irradiation energy of 16.56 Joule (J). Afterwards, the nano-assemblies solution was analyzed using dynamic light scattering (DLS, NanoBrook, Brookhaven Instruments, Holtsville, NY; the device is equipped with a 40 mW diode laser scattering angle of 90° at 25° C.). The results are summarized in the following table as mean±standard deviation.

| Samples | Size (nm) | PDI |
|---|---|---|
| Nano-assemblies based on conjugates of all trans retinal and glycine - BEFORE exposure to sunlight | 290.8 ± 1.1 | 0.05 ± 0.00 |
| Nano-assemblies based on conjugates of all trans retinal and glycine - AFTER exposure to sunlight | 273.9 ± 10.3 | 0.20 ± 0.05 |

There were only slight changes in size and PDI of the nano-assemblies based on conjugates of all trains retinal and glycine after 2 h exposure to sunlight. This means that the nano-assemblies were stable under the tested conditions.

6. Oxidation Stability Study

The all trans retinoic acid (ATRA) loaded nano-assemblies based on conjugates of all trans retinal and glycine made in Example 3 were first diluted in distilled water at 50% (w/v). The ATRA loaded nano-assemblies solution was then mixed with $H_2O_2$ solution (30% in water) at the volume ratio of nano-assemblies solution to $H_2O_2$ solution of 9:1 (v/v). The mixture was kept for 30 min or 60 min at room temperature. The ATRA amount loaded in the nano-assemblies before and after mixing with $H_2O_2$ was analyzed using HPLC, and the data is expressed in percentages and summarized in the following table as mean±standard deviation.

| Samples | Percentage (%) of ATRA amount loaded in the nano-assemblies |
|---|---|
| ATRA loaded nano-assemblies based on conjugates of all trans retinal and glycine - BEFORE mixing with $H_2O_2$ | 100 ± 0 |
| ATRA loaded nano-assemblies based on conjugates of all trans retinal and glycine - 30 min AFTER mixing with $H_2O_2$ | 100 ± 0 |
| ATRA loaded nano-assemblies based on conjugates of all trans retinal and glycine - 60 min AFTER mixing with $H_2O_2$ | 100 ± 0 |

The percentage of ATRA amount loaded in the nano-assemblies is calculated using the equation (III)

$$\text{Percentage of } ATRA \text{ amount loaded in the nano-assemblies} = \frac{ATRA\ \text{mass}_{detected}}{ATRA\ \text{mass}_{before\ mixing\ with\ H_2O_2}} \times 100\ (\%) \quad \text{(III)}$$

wherein the ATRA mass detected is the ATRA mass loaded or remained in the nano-assemblies determined using HPLC, and the ATRA mass before mixing with $H_2O_2$ is the initial ATRA mass loaded in the nano-assemblies which was determined in Example 3. The percentage of ATRA amount loaded in the nano-assemblies before mixing with $H_2O_2$ is always 100%.

After mixing with the strong oxidant $H_2O_2$ for 30 min and 60 min, the percentage of ATRA loaded in the nano-assemblies in both cases stayed stable at 100%. This indicates that the loading of ATRA in the nano-assemblies protected ATRA from $H_2O_2$.

7. Stability at Storage Conditions (Room Temperature (25-30° C.) and Ambient Pressure)

The nano-assemblies based on conjugates of all trans retinal and glycine were produced according to the procedure reported in Example 1 and then diluted in PBS to the concentration of 50 microgram/mL. The samples were then kept at room temperature (25-30° C.) and ambient pressure. The characteristics of the nano-assemblies, including hydrodynamic diameter, and polydispersity index (PDI) were determined at designated time points, 3 h, 7 d, 15 d, 21 d, and 28 d after the sample preparation, using dynamic light scattering (DLS, NanoBrook, Brookhaven Instruments, Holtsville, NY; the device is equipped with a 40 mW diode laser scattering angle of 90° at 25° C.). The results are summarized in the following table as mean±standard deviation.

| Time after sample preparation | Size (nm) | PDI |
|---|---|---|
| 3 h | 297.0 ± 6.5 | 0.04 ± 0.00 |
| 7 d | 240.0 ± 1.7 | 0.12 ± 0.02 |
| 15 d | 219.1 ± 3.9 | 0.10 ± 0.05 |
| 21 d | 217.9 ± 8.7 | 0.12 ± 0.02 |
| 28 d | 229.3 ± 4.0 | 0.17 ± 0.01 |

Despite slight changes, the characteristics of the nano-assemblies in aqueous media at room temperature and ambient pressure stayed stable over the study period.

The invention claimed is:

1. A nano-assembly comprising conjugates of the following formula (1)

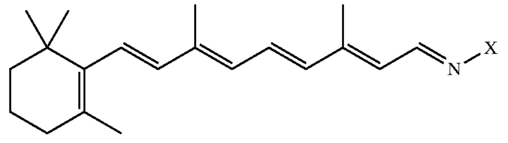

wherein X is selected from the group consisting of

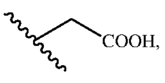
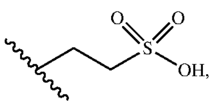

-continued

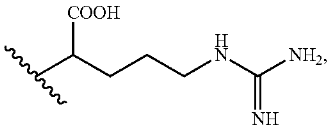

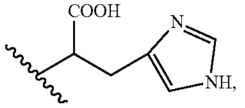

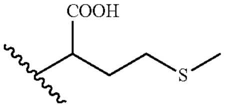
,

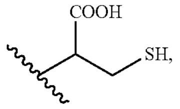

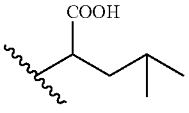
,

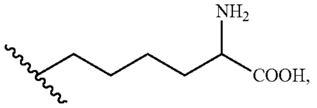

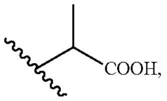

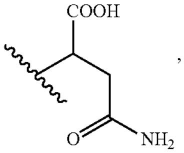
,

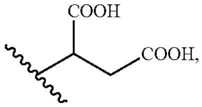

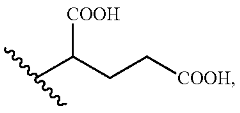

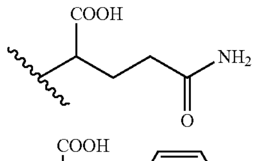
,

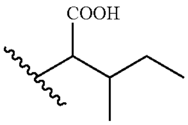
,

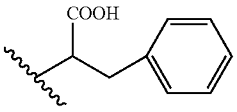
,

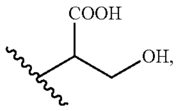

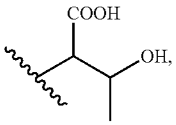

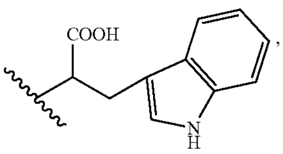
,

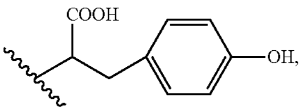
and

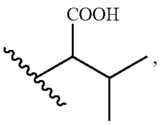
, and/or comprising conjugates of the following formula (4)

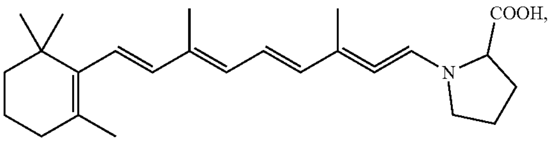 [SMILES: CC(=C=CN1CCCC1C(=O)O)/C=C/C=C(C)/C=C/C1=C(C)CCCC1(C)C]

2. The nano-assembly according to claim 1, wherein the nano-assembly comprises conjugates of formula (1).

3. The nano-assembly according to claim 1, wherein the nano-assembly further comprises conjugates of the following formula (5)

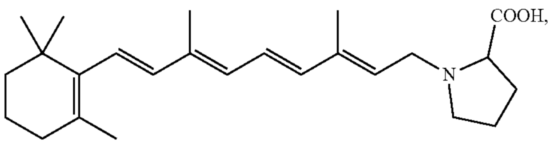 [SMILES: CC1=C(/C=C/C(C)=C/C=C/C(C)=C/CN2CCCC2C(=O)O)C(C)(C)CCC1]

conjugates of the following formula (6)

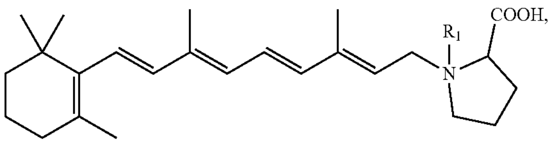

conjugates of the following formula (2)

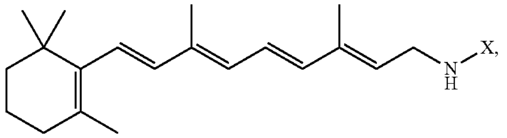

conjugates of the following formula (3)

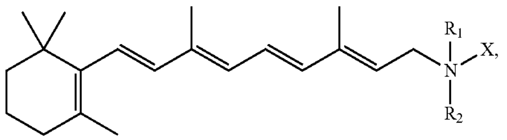

and/or combinations of two or more thereof, and wherein $R_1$ and $R_2$ are independently selected from the group consisting of —H, —$CH_3$, —$CH_2CH_3$, and —$CH_2CH_2$—(O—$CH_2CH_2)_m$—$R_3$, wherein m is in a range of from 1 to 20, and wherein $R_3$ is selected from the group consisting of —H, —OH, —$NH_2$, —SH, —COOH, and —$OCH_3$.

4. The nano-assembly according to claim 1, wherein the nano-assembly further comprises at least one additional retinoid compound, at least one additional vitamin E compound, at least one additional vitamin D compound, and/or at least one additional vitamin K compound bound to the nano-assembly by non-covalent interactions.

5. The nano-assembly according to claim 4, wherein the additional retinoid compound is all-trans retinoic acid.

6. The nano-assembly according to claim 1, wherein X is selected from the group consisting of

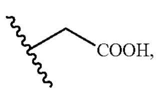

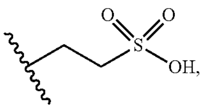 [SMILES: *CCS(=O)(=O)O]

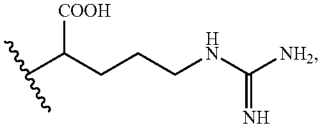

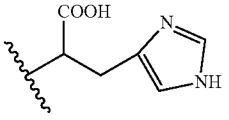
,

-continued

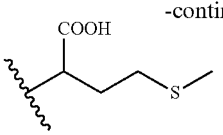,

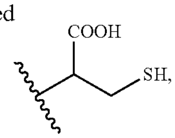

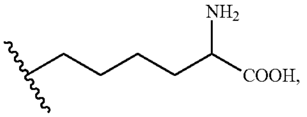

and

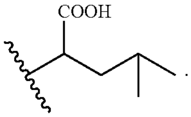.

7. The nano-assembly according to claim 1, comprising a first conjugate having formula (1), and further comprising a second conjugate having formula (1) wherein X of formula (1) is different from X of the second conjugate.

8. The nano-assembly according to claim 1, comprising conjugates of formula (1) wherein X is

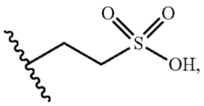

and further comprising conjugates of formula (1) wherein X is

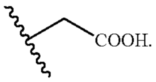 [SMILES: *CC(=O)O]

9. The nano-assembly according to claim 1, wherein a molar proportion of the conjugates of formula (1) is at least 50 mol% as compared to a total molar amount of conjugates constituting the nano-assembly.

10. A method of producing the nano-assembly of claim 1, the method comprising incubating a mixture of a retinoid compound and an amino acid in a mixture of a polar solvent A and a polar solvent B for a time of from 1 hour to 48 hours, and removing solvent B;

wherein solvent A has a higher polarity index as compared to solvent B.

11. The method according to claim 10, wherein a molar ratio of the retinoid compound and the amino acid in the mixture is in a range of from 1:50 to 1:1.

12. The method according to claim 10, wherein the retinoid compound is all trans retinal.

13. The method according to claim 10, wherein the polarity index of solvent A is at least 8.0.

14. The method of according to claim 10, further comprising addition of at least one additional retinoid compound to the mixture of the retinoid compound and the amino acid.

15. A method of treating dermatological diseases or conditions and/or pulmonary diseases or conditions, comprising administering a therapeutically effective amount of the nano-assembly according to claim 1 to a patient in need thereof.

16. A pharmaceutical composition comprising the nano-assembly according to claim 1, and a pharmaceutically acceptable carrier.

17. A method for managing or reducing stretch marks on skin (striae), smooth wrinkles, and fine lines comprising administering an effective amount of the nano-assembly according to claim 1 to a person in need thereof.

18. A method for treating androgenetic alopecia comprising administering an effective amount of the nano-assembly according to claim 1 to a person in need thereof.

* * * * *